US 6,677,501 B2

(12) United States Patent
Gabel et al.

(10) Patent No.: US 6,677,501 B2
(45) Date of Patent: Jan. 13, 2004

(54) $P_{2X7}$ RECEPTOR-DEFICIENT MICE AND USES THEREOF

(75) Inventors: Christopher A. Gabel, Ledyard, CT (US); Beverly H. Koller, Chapel Hill, NC (US)

(73) Assignee: Pfizer, Inc., Groton, CT (US)

( * ) Notice: Subject to any disclaimer, the term of this patent is extended or adjusted under 35 U.S.C. 154(b) by 0 days.

(21) Appl. No.: 09/875,318

(22) Filed: Jun. 6, 2001

(65) Prior Publication Data

US 2002/0007498 A1 Jan. 17, 2002

Related U.S. Application Data

(60) Provisional application No. 60/209,559, filed on Jun. 6, 2000.

(51) Int. Cl.[7] .................. A61K 67/027; C12N 15/00
(52) U.S. Cl. ..................... 800/18; 800/13; 800/14; 800/21; 800/22; 800/25; 435/455; 435/463; 435/325; 435/320.1
(58) Field of Search ................... 800/18, 21, 22, 800/25, 3, 13, 14; 435/455, 463, 320.1, 325

(56) References Cited

U.S. PATENT DOCUMENTS 6,133,434 A  10/2000  Buell et al. ................ 536/23.5

OTHER PUBLICATIONS

Mullins et.al.; Perspective Series: Moleclar Medicine in Genetically Engineered Animals, 1996, J. Clin. Invest., vol. 97, No. 7: 1557–1560.*

Moreadith et.al.; Gene targeting in embryonic stem cells: the new physiology and metabolism, 1997, J. Moi. Med. 75: 208–216.*

Capecchi; YTargeted Gene Replacement, 1994, Scientific American: 34–41.*

Chessell et.al.; Cloning and functional characterisation of the mouse P2X receptor; 1998, FEBS 439: 26–30.*

Sikora A et al., "Cutting edge: purinergic signaling regulates radical–mediated bacterial killing mechanisms in macrophages through a P2X7–independent mechanism" J Immunol. 1999 Jul. 15;163(2):558–61.

Guan Z et al., "Interleukin–1beta–induced cyclooxygenase–2 expression requires activation of both c–Jun NH2–terminal kinase and p38 MAPK signal pathways in rat renal mesangial cells" J Biol Chem. Oct. 30, 1998;273(44):286870–6.

Bhakdi S et al., "Effects of *Escherichia coli* hemolysin on human monocytes. Cytocidal action and stimulation of interleukin 1 release" J Clin Invest. Jun. 1990;85(6):1746–53.

Humphreys BD and Dubyak GR "Induction of the P2z/P2X7 nucleotide receptor and associated phospholipase D activity by lipopolysaccharide and IFN–gamma in the human THP–1 monocytic cell line" J Immunol. Dec. 15, 1996;157(12):5627–37.

Lomedico PT et al., "Cloning and expression of murine interleukin–1 cDNA in *Escherchia coli*" Nature. Nov. 29–Dec. 5, 1984;312(5993):458–62.

Bevilacqua MP et al., "Endothelial leukocyte adhesion molecule 1: an inducible receptor for neutrophils related to complement regulatory proteins and lectins" Science. Mar. 3, 1989; 243(4895):1160–5.

Griffiths RJ et al., "ATP induces the release of IL–1 from LPS–primed cells in vivo" J Immunol. Mar. 15, 1995;154(6):2821–8.

Miller DK et al., "Purification and characterization of active human interleukin–1 beta–converting enzyme from THP.1 monocytic cells" J Biol Chem. Aug. 25, 1993;268(24):18062–9.

Allen M et al., "Deficiency of the stress kinase p38alpha results in embryonic lethality: characterization of the kinase dependence of stress responses of enzyme–deficient embryonic stem cells" J Exp Med. Mar. 6, 2000;191(5):859–70.

Laliberte RE et al., "ATP treatment of human monocytes promotes caspase–1 maturation and externalization" J Biol Chem. Dec. 24, 1999;274(52):36944–51.

Ferrari D et al., "Extracellular ATP activates transcription factor NF–kappaB through the P2Z purinoreceptor by selectively targeting NF–kappaB p65" J Cell Biol. Dec. 29, 1997;139(97): 1635–43.

Sanz JM and Di Virgilio F "Kinetics and mechanisms of ATP–dependent IL–1 beta release from microglial cells" J Immunol. May 1, 2000;164(9):4893–8.

Mutini C et al., "Mouse dendritic cells express the P2X7 purinergic receptor: characteriation and possible participation in antigen presentation" J Immunol. Aug. 15, 1999;163(4):1958–65.

Baricordi OR et al., "Increased proliferation rate of lymphoid cells transfected with the P2X(7) ATP receptor"J Biol Chem. Nov. 19, 1999;274(47):33206–8.

Chiozzi P "Spontaneous cell fusion in macrophage cultures expressing high levels of the P2Z/P2X7 receptor" J Cell Biol. Aug. 11, 1997;138(3):697–706.

Virginio C et al., "Kinetics of cell lysis, dye uptake and permeability changes in cells expressing the rat P2X7 receptor" J Physiol. Sep. 1, 1999;519 Pt 2:335–46.

(List continued on next page.)

Primary Examiner—Deborah Crouch
Assistant Examiner—Thai-an N. Ton
(74) Attorney, Agent, or Firm—Hale & Dorr LLP

(57) ABSTRACT

The invention provides non-human, genetically-modified mammals and genetically modified animals cells having a functionally disrupted $P_{2X7}$ receptor gene. Also provided are methods for producing genetically modified mice in which one or both $P_{2X7}R$ alleles have been functionally inactivated.

6 Claims, 8 Drawing Sheets

OTHER PUBLICATIONS

Ferrari D et al., "P2Z purinoreceptor ligation induces activation of caspases with distinct roles in apoptotic and necrotic alterations of cell death" FEBS Lett. Mar. 19, 1999;447(1):71–5.

Sanz JM and Di Virgilio F "Kinetics and mechanism of ATP–dependent IL–1 beta release from microglial cells" J Immunol. May 1, 2000;164(9):4893–8.

Rassendren F et al., "The permeabilizing ATP receptor, P2X7. Cloning and expression of a human cDNA" Biol Chem. Feb. 28, 1997;272(9):5482–6.

Collo G et al., "Tissue distribution of the P2X7 receptor" Neuropharmacology. Sep. 1997;36(9):1277–83.

Michel AD et al., "Identification and characterization of an endogenous P2X7 (P2Z) receptor in CHO–K1 cells" Br J Pharmacol. Nov. 1998;125(6):1194–201.

Steinberg TH et al., "ATP4– permeabilizes the plasma membrane of mouse macrophages to fluorescent dyes" J Biol Chem. Jun. 25, 1987;262(18):8884–8.

Greenberg S et al., "Extracellular nucleotides mediate Ca2+ fluxes in J774 macrophages by two distinct mechanisms" J Biol Chem. Jul. 25, 1988;263(21):10337–43.

North RA "Families of ion channels with two hydrophobic segments" Curr Opin Cell Biol. Aug. 1996;8(4):474–83. Review.

Di Virgilio F "The P2Z purinoceptor: an intriguing role in immunity, inflammation and cell death" Immunol Today. Nov. 1995;16(11):524–8. Review.

Perregaux DG et al., "Tenidap and other anion transport inhibitors disrupt cytolytic T lymphocyte–mediated IL–1 beta post–translational processing" J Immunol. Jul. 1, 1996;157(1):57–64.

Walter P and Johnson AE "Signal sequence recognition and protein targeting to the endoplasmic reticulum membrane" Annu Rev Cell Biol. 1994;10:87–119. Review.

Wiley JS and Dubyak GR "Extracellular adenosine triphosphate increases cation permeability of chronic lymphocytic leukemic lymphocytes" Blood. Apr. 1989;73(5):1316–23.

Walev I et al., "Potassium–inhibited processing of IL–1 beta in human monocytes" EMBO J. Apr. 18, 1995;14(8):1607–14.

Perregaux D et al., "IL–1 beta maturation: evidence that mature cytokine formation can be induced specifically by nigericin" J Immunol. Aug. 15, 1992;149(4):1294–303.

March CJ et al., "Cloning, sequence and expression of two distinct human interleukin–1 complementary DNAs" Nature. Jun. 20–26, 1985;315(6021):641–7.

Thornberry NA et al., "A novel heterodimeric cysteine protease is required for interleukin–1 beta processing in monocytes" Nature. Apr. 30, 1992;356(6372):768–74.

Hogquist KA et al., "Interleukin 1 is processed and released during apoptosis" Proc Natl Acad Sci U S A. Oct. 1, 1991;88(19):8485–9.

Foresta C et al., "Mechanism of human sperm activation by extracellular ATP" Am J Physiol. Jun. 1996;270(6 Pt 1):C1709–14.

Flannery CR et al., "Effects of culture conditions and exposure to catabolic stimulators (IL–1 and retinoic acid) on the expression of matrix metalloproteinases (MMPs) and disintegrin metalloproteinases (ADAMs) by articular cartilage chondrocytes" Matrix Biol. Jun. 1999;18(3):225–37.

Ayala JM et al., "IL–1 beta–converting enzyme is present in monocytic cells as an inactive 45–kDa precursor" J Immunol. Sep. 15, 1994;153(6):2592–9.

Gray PW et al., "Two interleukin 1 genes in the mouse: cloning and expression of the cDNA for murine interleukin 1 beta" J Immunol. Dec. 1, 1986;137(11):3644–8.

Slack J et al., "Independent binding of interleukin–1 alpha and interleukin–1 beta to type I and type II interleukin–1 receptors" J Biol Chem. Feb. 5, 1993;268(4):2513–24.

Lammas DA et al., "ATP–induced killing of mycobacteria by human macrophages is mediated by purinergic P2Z(P2X7) receptors" Immunity. Sep. 1997;7(3):433–44.

Mosley B et al., "The interleukin–1 receptors binds the human interleukin–1 alpha precursor but not the interleukin–1 beta precursor" J Biol Chem. Mar. 5, 1987;262(7):2941–4.

Perregaux D and Gabel CA "Interleukin–1 beta maturation and release in response to ATP and nigericin" J Biol Chem. May 27, 1994;269(21):15195–203.

Cerretti DP et al., "Molecular cloning of the interleukin–1 beta converting enzyme" Science. Apr. 3, 1992;256(5053):97–100.

McNiff PA et al., "Synovial fluid from rheumatoid arthritis patients contains sufficient levels of IL–1 beta and IL–6 to promote production of serum amyloid A by Hep3B cells" Cytokine. Feb. 1995;7(2):209–19.

Murgia M et al, "Characterization of the cytotoxic effect of extracellular ATP in J774 mouse macrophages" Biochem J. Dec. 15, 1992;288 ( Pt 3):897–901.

Surprenant A et al., "The cytolytic P2Z receptor for extracellular ATP identified as a P2X receptor (P2X7)" Science. May 3, 1996;272(5262):735–8.

\* cited by examiner

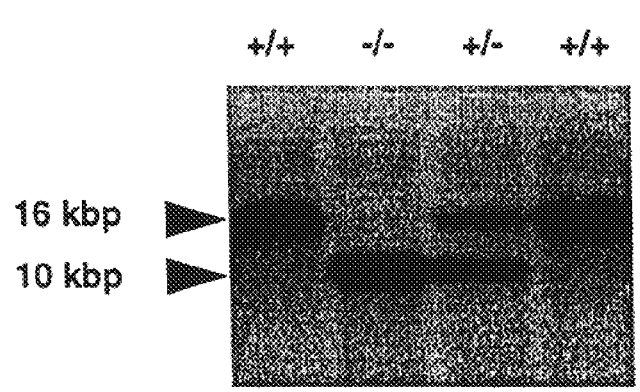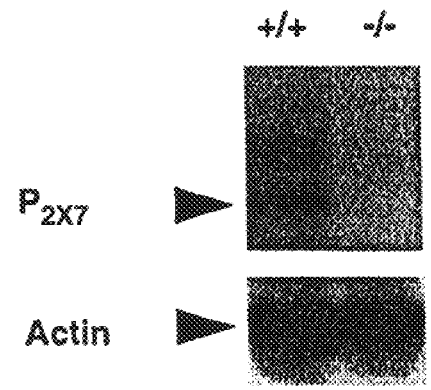
FIG. 2A
FIG. 2B

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: synthetic DNA

<400> SEQUENCE: 1
cggcgtgcgt tttgacatcc t                                      21

<210> SEQ ID NO 2
<211> LENGTH: 17
<212> TYPE: DNA
<213> ORGANISM: Artificial Sequence
<220> FEATURE:
<223> OTHER INFORMATION: synthetic DNA

<400> SEQUENCE: 2
agggccctgc ggttctc                                           17
```

P$_{2X7}$ RECEPTOR-DEFICIENT MICE AND USES THEREOF

The present invention relates to non-human, genetically modified mammals and genetically modified animal cells having a disruption in a P$_{2x7}$ receptor gene locus that prevents or reduces endogenous P$_{2x7}$ receptor function. This application claims the benefit of U.S. Provisional Application No. 60/209,559, filed Jun. 6, 2000.

FIELD OF THE INVENTION

BACKGROUND OF THE INVENTION

Cell surface ATP receptors can be divided into the metabotropic receptor family (P2Y/P2U) and the ionotropic receptor family (or the P$_{2x}$ receptor family). Metabotropic receptor family members are G-protein coupled receptors and ionotropic receptor family members are ligand-gated channels. There are eleven metabotropic receptor family members and seven ionotropic receptor family members, P$_{2x1}$R to P$_{2x7}$R.

The P$_{2x7}$ receptor (P$_{2x7}$R), like other members of the P2x receptor family, is an ATP-gated ion channel (Surprenant et al. (1996) *Science* 272:735–738; Rassendren et al. (1997) *J. Biol. Chem.* 272:5482–5486; Michel et al. (1998) *Br. J. Pharmacol.* 125:1194–1201). The P$_{2x7}$R, however, demonstrates attributes that clearly distinguish it from other members of the family. For example, the P$_{2x7}$R requires levels of ATP in excess of 1 mM to achieve activation whereas other P$_{2x}$ receptors activate at ATP concentrations $\leq 100$ $\mu$M (Greenberg et al. (1988) *J. Biol. Chem.* 263:10337–10343; Steinberg et al. (1987) *J. Biol. Chem.* 262:8884–8888): the higher concentration requirement reflects, in part, the preference of the P$_{2x7}$R for ATP$^{4-}$ as its ligand and the relatively low abundance of this species in media containing physiological concentrations of divalent cations (e.g., Ca$^{2+}$ and Mg$^{2+}$). An additional unique feature of the P$_{2x7}$R is found in its conductance properties. All P$_{2x}$ receptors demonstrate non-selective channel-like properties following ligation, but the channels formed by the P$_{2x7}$R rapidly transform to "pores" that allow passage of solutes as large as 900 daltons (Steinberg et al. (1987) *J. Biol. Chem.* 262:8884–8888; Virgihio et al. (1999) *J. Physiol.* 519:335–346). Molecular details of this transformation remain to be described, but domain swapping and deletion experiments have suggested that the carboxy terminal domain of the P$_{2x7}$R participates in pore complex formation; the carboxy terminal domain is significantly longer than the comparable domains in the other P$_{2x}$ receptors (North (1996) *Current Opin. Cell Biol.* 8:474–483). Possibly as a consequence of this pore-like activity, continuous ligation of the P$_{2x7}$ receptor for times greater than 15 minutes can lead to cell death (Di Virgilio (1995) *Immunol. Today* 16:524–528; Murgia et al. (1992) *Biochem. J.* 288:897–901; Ferrari et al. (1999) *FEBS Let.* 447:71–75).

The P$_{2x7}$R displays a restricted cellular distribution, being observed primarily in cells of hematopoietic origin including monocytes and macrophages and some lymphocyte populations (Di Virgilio (1995) *Immunol. Today* 16:524–528; Collo et al. (1997) *Neuropharmacol.* 36:1277–1283). The receptor also has been reported to exist on microglial cells (Sanz et al. (2000) *J. Immunol.* 164:4893–4898), some cancer cells (Wiley et al. (1989) *Blood* 73:1316–1323), sperm (Foresta et al. (1996) *Am J. Physiol.* 270:C1709–C1714), and dendritic cells (Mutini et al. (1999) *J. Immunol.* 163:1958–1965).

The P$_{2x7}$R has been reported to participate in a diverse list of cellular activities including lymphocyte proliferation (Baricordi et al. (1999) *J. Biol. Chem.* 274:33206–33208), fertilization (Foresta et al. (1996) *Am J. Physiol.* 270:C1709–C1714), giant cell formation (Chiozzi et al. (1997) *J. Cell Biol.* 138:697–706), cell death (Murgia et al. (1992) *Biochem. J.* 288:897–901; Ferrari et al. (1999) *FEBS Let.* 447:71–75), killing of invading mycobacteria (Latumas et al. (1997) *Immunity* 7:433–444), and IL-1 posttranslational processing (Hogquist et al. (1991) *Proc. Natl. Acad. Sci.* (*USA*) 88:8485–8489; Perregaux et al. (1994) *J. Biol. Chem.* 269:15195–15203). Further, ligation of the P$_{2x7}$R has been associated with activation of phospholipase D and activation of some forms of NF-$\epsilon$B (Humphreys et al. (1996) *J. Immunol.* 157:5627–5637; Ferrari et al. (1997) *J. Cell Biol.* 139:1635–1643).

One of the most intriguing activities attributed to the P$_{2x7}$R is its ability to induce posttranslational processing of proIL-1 (Sanz et al. (2000) *J. Immunol.* 164:4893–4898; Hogquist et al. (1991) *Proc. Natl. Acad. Sci.* (*USA*) 88:8485–8489; Perregaux et al. (1994) *J. Biol. Chem.* 269:15195–15203). Interleukin (IL)-1 is a multipotential inflammatory mediator produced in abundance by activated monocytes and macrophages. The administration of IL-1 to animals has been shown to initiate an inflammatory response, produce fever, and promote tissue degradation. Further, elevated levels of IL-1 have been detected in patients suffering from a number of chronic disorders, including rheumatoid arthritis, Alzheimer's disease, and acute myelocytic leukemia (McNiff et al. (1995) *Cytokine* 7:209; Gray et al. (1986) *J. Immunol.* 137:3644; Lomedico et al. (1984) *Nature* 312:458).

When IL-1 is released from cells, it binds to receptors on target cells and elicits complex signaling cascades leading to the upregulation of gene products that contribute to an inflammatory state including matrix metalloproteinases, cyclooxygenase-2, IL-6, and cellular adhesion molecules (Flannery et al. (1999) *Matrix Biol.* 18:225–237; Guzn et al. (1998) *J. Biol. Chem.* 273:28670–28676; Allen et al. (2000) *J. Exp. Med.* 191:859–869; Bevilacqua et al. (1989) *Science* 243:1160–1164). Two distinct gene products, IL-1$\alpha$ and IL-1$\beta$, contribute to IL-1 biological activity. The amino acid sequences of IL-1a and IL-1$\beta$ are only 25% identical yet these two polypeptides bind to the same receptors on target cells (Slack et al. (1993) *J. Biol. Chem.* 268:2513–2524). Human EL-1$\alpha$ and IL-$\beta$ are both initially produced as 31 kDa procytokines containing amino terminal extensions that are subsequently removed by proteolysis. In the case of proIL-1$\alpha$, the propolypeptide and the 17 kDa cleavage product display equivalent signaling activity indicating that proteolytic cleavage is not necessary to generate a receptor-competent ligand. In contrast, proIL-1$\beta$ does not bind to the signaling IL-1 receptor (Mosley et al. (1987) *J. Biol. Chem.* 262:2941–2944), and cleavage by caspase-1 is necessary to generate the mature 17 kDa signaling-competent form of this cytokine (Cerretti et al. (1992) *Science* 256:97–100; Thornberry et al. (1992) *Nature* 356:768–774).

The two forms of IL-1 share another very unusual attribute, both proIL-1$\alpha$ and proIL-1$\beta$ are synthesized without a signal sequence (March et al. (1985) *Nature* 315:641–647), the peptide epitope required to direct nascent polypeptides to the endoplasmic reticulum (Walter et al. (1994) *Ann. Rev. Cell Biol.* 10:87–119). As a result, newly synthesized proIL-1$\alpha$ and proIL-1$\beta$ accumulate within the cytoplasmic compartment of producing cells rather than being sequestered to the secretory apparatus. Caspase-1 also is produced as a cytosol-localized proenzyme, the 45 kDa propolypeptide must be proteolytically processed to generate the 20 kDa and 10 kDa subunits which constitute the mature active protease (Thornberry et al. (1992) *Nature* 356:768–774; Miller et al. (1993) *J. Biol. Chem.* 268:18062–18069; Ayala et al. (1994) *J. Immunol.* 153:2592–2599). In activated monocytes and macrophages, therefore, proIL-1β and procaspase-1 co-exist within the cytoplasm. Mechanisms that control activation of procaspase-1, and in turn cleavage of proIL-1β, are not well understood. Recent studies, however, have provided evidence that proteolytic processing IL-1β and release of the mature cytokine product extracellularly do not proceed constitutively. Rather, the post-translational processing of proIL-1 requires that lipopolysaccharide-(LPS)-activated monocytes and/or macrophges encounter an external stimulus that promotes activation of procaspase-1, cleavage of proIL-1β, and release of the 17 kDa cytokine (Miller et al. (1995) *J. Immunol.* 154:1331–1338; Laliberte et al. (1999) *J. Biol. Chem.* 274:36944–36951; Sanz et al. (2000) *J. Immunol.* 164:4893–4898). Stimuli that function in vitro to promote IL-1 posttranslational processing by LPS-activated monocytes and/or macrophages include ATP, nigericin, cytolytic T-cells, bacterial toxins and hypotonic stress (Bhakdi et al. (1990) *J. Clin. Invest.* 85:7988–7992; Hogquist et al. (1991) *Proc. Natl. Acad. Sci. (USA)* 88:8485–8489; Perregaux et al. (1992) *J. Immunol.* 149:1294–1303; Perregaux et al. (1994) *J. Biol. Chem.* 269:15195–15203; Perregaux et al. (1996) *J. Immunol.* 157:57–64; Walev et al. (1995) *EMBO J.* 14:1607–1614). This requirement for secretion stimulus is not restricted to cells in culture; mouse peritoneal macrophages produce proIL-1β in response to intraperitoneal (i.p.) injection of LPS, but release little cytokine extracellularly (Griffiths et al. (1995) *J. Immunol.* 154:2821–2828). Subsequent i.p. injection of ATP, however, stimulates generation of large quantities of extracellular mature IL-1β (Griffiths et al. (1995) *J. Immunol.* 154:2821–2828).

SUMMARY OF THE INVENTION

The present invention provides non-human, genetically-modified mammals and animal cells containing a disrupted $P_{2x7}R$ gene that prevents or reduces endogenous $P_{2x7}R$ function.

In one aspect, the invention provides a genetically-modified, non-human mammal, wherein the genome of the mammal comprises a genetic modification to a copy of the $P_{2x7}R$ gene that results in disrupted $P_{2x7}R$ gene function from the modified gene. In one embodiment, the mammal is heterozygous for the modified $P_{2x7}R$ gene. In another embodiment, the mammal is homozygous for the modified $P_{2x7}R$ gene.

In preferred embodiments, the mammal is a rodent, such as a mouse. In some embodiments, the mouse is homozygous for the modified $P_{2x7}R$ gene and exhibits reduced ATP-stimulated intracellular translocation of macromolecules. In other embodiments, the mouse is homozygous for the modified $P_{2x7}R$ gene and exhibits reduced ATP-stimulated interleukin-(IL)-1α, IL-1β, or IL-18 posttranslational processing or reduced ATP-stimulated IL-6 production.

In some embodiments, the $P_{2x7}R$ gene is disrupted by homologous recombination, and in other embodiments, the $P_{2x7}R$ gene is disrupted by the insertion of a gene trapping vector.

The invention provides, in another aspect, a method for producing a genetically-modified mouse comprising a disrupted $P_{2x7}R$ gene. In this method, a nucleic acid molecule is introduced into a mouse embryonic stem cell, wherein the nucleic acid molecule inserts into the $P_{2x7}R$ gene, thereby disrupting the gene. In one embodiment of the method of the invention, the nucleic acid molecule disrupts the $P_{2x7}R$ gene by homologous recombination. In another embodiment, the nucleic acid molecule disrupts the $P_{2x7}R$ gene by the insertion of a gene trapping vector. The mouse embryonic stem cell containing the introduced nucleic acid is then introduced into a mouse embryo, which is then transplanted into a pseudopregnant mouse. The embryo containing the introduced mouse embryonic stem cell is allowed to develop to term, after which a genetically-modified mouse is identified whose genome comprises a disruption of a $P_{2x7}R$ gene.

In another aspect, the invention provides an isolated nucleic acid molecule comprising a $P_{2x7}R$ gene targeting construct. Upon introduction of the targeting construct into a cell, the construct recombines with a $P_{2x7}R$ gene in the cellular genome, thereby inserting itself at the $P_{2x7}R$ gene locus and disrupting $P_{2x7}R$ gene function in the cell.

The invention provides, in yet another aspect, a genetically-modified animal cell comprising a genetic modification in at least one copy of $P_{2x7}R$ gene in the genome of the cell, the genetic modification resulting in disrupted function in the modified copy of $P_{2x7}R$ gene. In some embodiments, the cell is a mammalian cell. In a preferred embodiment, the cell is an embryonic stem cell. In some embodiments, the cell is derived from a genetically-modified, non-human mammal or non-human mammalian embryo. In some embodiments, the cell is heterozygous for the modified $P_{2x7}R$ gene, and in other embodiments the cell is homozygous for the modified $P_{2x7}R$ gene.

Various terms used herein are defined as stated below.

By a non-human mammal or an animal cell that is "genetically-modified" is meant such a mammal or cell having a modification in a gene of interest which was introduced into the non-human mammal or cell, or a progenitor mammal or cell, by genetic engineering. The non-human mammal or cell is heterozygous or homozygous for the modified gene. In a genetically-modified, non-human mammal, it is preferred that all somatic cells and germline cells contain the modified gene.

This modification disrupts $P_{2x7}R$ gene function and features the insertion of a foreign nucleic acid sequence into the $P_{2x7}R$ gene locus, either alone or in combination with a deletion of the endogenous $P_{2x7}R$ gene sequence, and the modification can occur within any region of the $P_{2x7}R$ gene, e.g., in an enhancer, promoter, regulator region, noncoding region, coding region, intron, or exon.

By a nucleic acid sequence that is "exogenous" or "foreign" to a $P_{2x7}R$ gene is meant a sequence that is non-naturally occurring in the $P_{2x7}R$ gene. Portions of the exogenous sequence may be either "homologous" or "heterologous" to $P_{2x7}R$ gene. By "homologous" is meant a sequence that is related to a $P_{2x7}R$ gene to a degree sufficient to allow in vivo hybridization. By contrast, a "heterologous" sequence is unrelated to $P_{2x7}R$ gene and does not hybridize in vivo with a $P_{2x7}R$ gene.

By "disrupted $P_{2x7}R$ gene function" is meant a decrease in the $P_{2x7}R$ polypeptide activity encoded by the modified $P_{2x7}R$ gene. When the genetic modification in a non-human mammal or animal cell effectively eliminates all wild type copies of the $P_{2x7}R$ gene (e.g., the non-human mammal or animal cell is homozygous for the $P_{2x7}R$ gene disruption or the only wild type copy of the $P_{2x7}R$ gene originally present in the genome of the non-human mammal or animal cell is now disrupted), then the $P_{2x7}R$ gene disruption results in a statistically significant reduction in the $P_{2x7}R$ polypeptide activity, as compared to the wild type, non-human mammal or animal cell of the same strain or type. This reduction in $P_{2x7}R$ polypeptide activity results from reduced expression of the $P_{2x7}R$ gene (i.e., reduced $P_{2x7}R$ mRNA levels produce reduced levels of $P_{2x7}R$ polypeptide) and/or because the modified $P_{2x7}R$ gene encodes a mutated polypeptide with reduced function compared to a wild type $P_{2x7}R$ polypeptide. Preferably, the activity of the $P_{2x7}R$ polypeptide is reduced to about 50% or less of wild type levels, more preferably, to about 25% or less, and, even more preferably, to about 10% or less of wild type levels. Most preferably, the $P_{2\times7}R$ polypeptide activity is nondetectable in the genetically modified, non-human mammal or animal cell (i.e., the $P_{2\times7}R$ gene disruption results in a null mutation).

By "pseudopregnant" mouse is meant a female mouse with hormone levels comparable to a pregnant mouse and sufficient to maintain a pregnancy. A pseudopregnant mouse is prepared by mating a female mouse in natural estrus with a vasectomized or genetically sterile male mouse.

By "reduced" is meant a statistically significant decrease (i.e., p<0.1).

By "modulates" is meant a statistically significant increase or decrease in level.

By "$P_{2\times7}R$ polypeptide activity" or "$P_{2\times7}R$-like activity" is meant an increased ATP-stimulated cell permeability and an increased accumulation of a macromolecule, e.g., a dye macromolecule such as YoPro Yellow, an increase in ATP-stimulated IL-1α, IL-1β, or IL-18 posttranslational processing in activated inflammatory cells (e.g., activated by lipopolysaccharide treatment or cytokine treatment, such as tumor necrosis factor-α), an increase in ATP-stimulated IL-6 production in inflammation-induced cells, or lymphoproliferation.

The term "animal cell" is meant to include a cell in an immortalized cell line, in a primary cell preparation, or otherwise derived from an animal. Preferably, the animal is a mammal such as a human, mouse, or rat.

BRIEF DESCRIPTION OF THE DRAWINGS

The foregoing and other aspects of the present invention, the various features thereof, as well as the invention itself may be more fully understood from the following description, when read together with the accompanying drawings in which:

FIG. 2A is a representation of a Southern blot of the $P_{2\times7}R$ genomic region in $P_{2\times7}R^{+/+}$, $P_{2\times7}R^{+/-}$ and $P_{2\times7}R^{-/-}$ mice in which DNA from pups derived from a heterozygous mating. DNA was digested with Eco RV and hybridized with the probe indicated by a dotted line in FIG. 1. This probe detects a 16 Kb band from the endogenous locus and a 10 Kb band from the targeted locus;

FIG. 2B is a representation of a Northern blot showing the absence of $P_{2\times7}R$ RNA expression in $P_{2\times7}R^{-/-}$ mice. RNA from cultured bone marrow derived mast cells from $P_{2\times7}R^{+/+}$ and $P_{2\times7}R^{-/-}$ mice was analyzed by Northern blot analysis for $P_{2\times7}R$ expression using a cDNA probe specific for the $P_{2\times7}R$ mRNA. Equal loading of the lanes and the integrity of the mRNA obtained from the $P_{2\times7}R^{-/-}$ cells were confirmed by analysis of the Northern blot with an actin specific probe;

DETAILED DESCRIPTION

Figure 1:
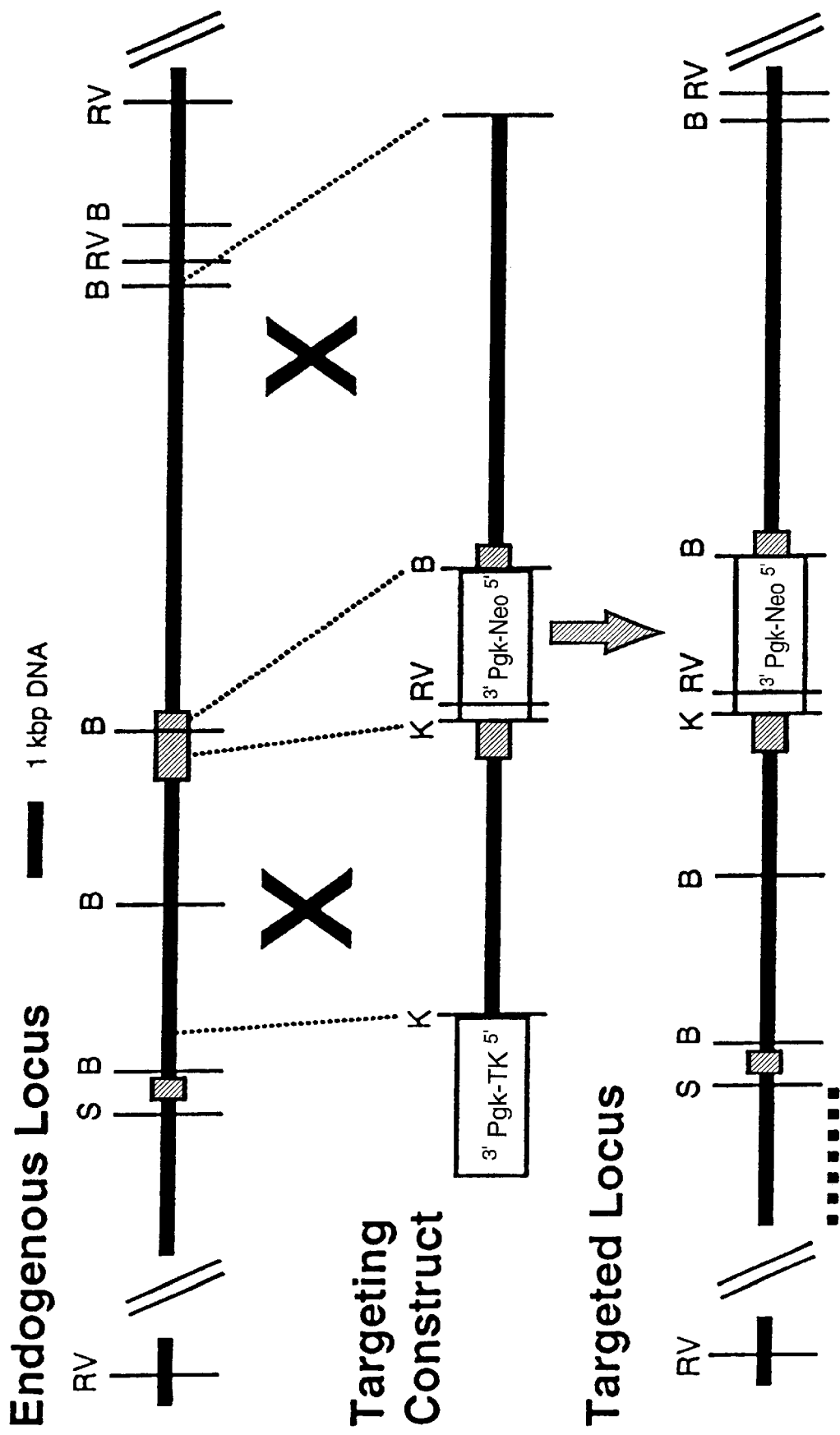
FIG. 1 is a diagrammatic representation of a homologous recombination event occurring between an endogenous locus (the murine $P_{2\times7}R$ genomic locus) and a targeting vector. The top line represents the $P_{2\times7}R$ genomic locus. The middle line depicts the targeting vector with a KpnI-BamHI (B) fragment (the neomycin resistance gene) inserted into an exon directly after the Arg$^{505}$ codon. The targeted locus after homologous recombination is shown at the bottom; filled gray boxes indicate exons and labeled boxes indicate the PGK-TK and PGK-Neo selection cassettes. Homologous recombination of the targeting vector with the endogenous $P_{2\times7}$ gene disrupts the carboxy (COOH) terminal coding region of the $P_{2\times7}$ gene. Relevant restriction sites are abbreviated as follows, B, BamHI; TV, EcoRV; K, KpnI; S, SalI.

The patent and scientific literature referred to herein establishes the knowledge that is available to those with skill in the art. The issued U.S. patents, allowed applications, published foreign applications, and references cited herein are hereby incorporated by reference.

The present invention provides non-human, genetically modified animals, preferably genetically modified mice, which harbor a disruption in a $P_{2x7}R$ gene locus that functionally disrupts an endogenous $P_{2x7}R$ gene locus. The invention encompasses non-human, genetically modified animals which are heterologous ($P_{2x7}R^{+/-}$) or homozygous ($P_{2x7}R^{-/-}$) for $P_{2x7}R$ gene disruption. Preferably, the germline and somatic cells of the non-human genetically modified animals contain the disruption of the $P_{2x7}R$ gene locus.

The present invention also provides animal cells, including human cells, having a disruption in a $P_{2x7}R$ gene locus. Preferably, the disruption prevents the expression of the endogenous $P_{2x7}R$ gene. The invention encompasses embryonic stem cells that are heterozygous or homozygous for $P_{2x7}R$ gene disruption. Preferably, the embryonic stem cells are mouse embryonic stem cells. In an alternative embodiment, the genetically modified cells are human cells. The present invention also provides cells obtained from a non-human, genetically modified mammal that is heterologous or homozygous for $P_{2x7}R$ gene disruption. These cells may be in the form of primary cell preparations or immortalized cell lines.

The non-human, genetically modified animals contemplated by the present invention generally include any non-human mammals which encode a $P_{2x7}R$ gene or homolog thereof. Such non-human genetically modified animals may include, for example, genetically modified pigs, genetically modified rats, genetically modified rabbits, genetically modified cattle, genetically modified goats, and other genetically modified mammalian species known in the art, such as chimpanzee. Preferably, the animals are mice and most preferably the animals are non-human primates.

Gene targeting, which is a method of using homologous recombination to modify a mammalian genome, can be used to introduce changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert additional sequences, such as a positive selection marker, into coding elements of the target gene, thereby functionally disrupting it. Targeting constructs usually are insertion-type ("knock in;" see, e.g., Hanks et al. (1995) *Science* 269:679–682; and Wang et al., (1996) *Nature* 379:823–825) or replacement-type constructs ("knock out;" Hasty et al. (1991) *Mol. Cell. Biol.* 11:4509).

The non-human, genetically modified animals and cells that have at least one $P_{2x7}R$ locus inactivated can be prepared by any of several techniques that are well established in the art including, but not limited to, those cited herein. For example, techniques such as homologous recombination gene trapping, or mutagenesis induced chemically or by irradiation may be used, as described in U.S. Pat. No. 5,464,764; U.S. Pat. No. 5,859,312; Shastry (1994) *Mol. Cell. Biochem.* 136:171–182; Shastry, B. S. (1995) *Experentia* 51:1028–1039; Bronson et al. (1994) *J. Biol. Chem.* 264:27155–27158; Capecchi (1989) *Science* 244:1288–1292; Smithies et al. (1995) *Proc. Natl. Acad. Sci.* (*USA*) 92:5266–5272; Gatherer, D. (1993) *Dev. Growth Diff.* 35:365–370; and Rossant (1991) *Curr. Opin. Genet. Dev.* 1:236–240. In general, cells that have at least one $P_{2x7}R$ locus inactivated may be engineered by:

(1) constructing a targeting vector comprising a cloning vector and a DNA fragment containing at least one positively selectable marker gene (positive selection marker), flanked by two regions that are homologous to the animal's $P_{2x7}R$ gene or genomic locus and which are in the same 5' to 3' orientation to one another (referred to as the regions of homology);

(2) including in the targeting vector a negatively selectable marker gene (negative selection marker) adjacent to one of the regions of homology. This negatively selectable marker may increase the likelihood of recovering the desired homologous recombination event (deleting a portion of the $P_{2x7}R$ gene) but it is not required;

(3) transfecting $P_{2x7}R$ wild-type animal cells with the targeting vector of step (2);

(4) selecting the transfected cells from step 3 for the marker(s) on the vector; and (5) screening for cells with at least one $P_{2x7}R$ locus inactivated from those cells in step (4) which are found to contain or express said positive selection marker(s), and not express said negative selection marker(s).

General principles regarding the construction of targeting constructs are reviewed in Bradley et al. (*BioTechnol.* (1992) 10:534). The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region. $P_{2x7}R$ targeting constructs of the invention have a polynucleotide sequence comprising: (1) at least one $P_{2x7}R$ homology region having a sequence that is substantially identical to or substantially complementary to a sequence present in a host cell endogenous $P_{2x7}R$ gene locus; and (2) a targeting region which becomes integrated into a host cell endogenous $P_{2x7}R$ gene locus by homologous recombination between a targeting construct homology region and said endogenous $P_{2x7}R$ gene locus sequence. Typically, targeting constructs of the invention are used for functionally disrupting an endogenous $P_{2x7}R$ gene and comprise at least two homology regions separated by a nonhomologous sequence which contains an expression cassette encoding a selectable marker, such as neo (Smith and Berg (1984) *Cold Spring Harbor Symp. Quant. Biol.* 49:171; Sedivy and Sharp (1989) *Proc. Natl. Acad. Sci.* (*USA*) 86:227; Thomas and Capecchi (1987) *Cell* 51:503.

Other markers that could be used in the targeting construct include hyg, hisD, gpt, ble, hprt, β-galactosidase, β-lactamase, firefly luciferase, or green fluorescent protein (see, e.g., Capecchi et al., U.S. Pat. No. 5,464,764; Capecchi (1989) *Science* 244:1288–92; *Current Protocols in Cytometry*, Units 9.5 and 9.6, John Wiley & Sons, New York, N.Y., 2000).

In a preferred embodiment, a targeting construct comprises, in order: (1) a first homology clamp having a sequence substantially identical to a sequence within about 3 kilobases upstream (i.e., in the direction opposite to the translational reading frame of the $P_{2x7}R$ gene exons) of an exon of an endogenous $P_{2x7}R$ gene; (2) a replacement region comprising a positive selection cassette having a promoter driving transcription of a neo gene; (3) a second homology clamp having a sequence substantially identical to a sequence within about 3 kilobases downstream of said exon of said endogenous $P_{2x7}R$ gene; and (4) a negative selection cassette. Such a targeting construct is suitable for double-crossover replacement recombination which deletes a portion of the endogenous $P_{2x7}R$ gene locus spanning said exon and replaces it with the replacement region having the positive selection cassette. If the deleted exon is essential for expression of a functional $P_{2\times7}R$ gene product, the resultant exon-depleted allele is functionally disrupted and is termed a null allele.

Targeting constructs or portions thereof comprising at least one portion of a nucleotide sequence that is substantially homologous to a sequence present in or flanking an endogenous $P_{2\times7}R$ gene locus integrate by homologous recombination and result in a functional disruption in the expression of $P_{2\times7}R$ from the gene locus. If the targeting construct is a "hit-and-run" or "in-and-out" type construct (Valancius and Smithies (1991) *Mol. Cell. Biol.* 11: 1402; Donehower et al. (1992) *Nature* 356:215; Donehower et al. (1991) *J. NIH Res.* 3:59), the $P_{2\times7}R$ targeting region is only transiently incorporated into the endogenous $P_{2\times7}R$ gene locus and is eliminated from the host genome by selection. A $P_{2\times7}R$ targeting region may comprise a sequence that is substantially homologous to an endogenous $P_{2\times7}R$ gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome; nor does it necessarily indicate that the polynucleotide comprises a complete structural gene sequence. As used in the art, the term "targeting construct" is synonymous with the term "targeting transgene" as used herein. Targeting constructs are generally double-stranded DNA molecules, most usually linear.

A "homology region" or "homology clamp" is a segment (i.e., a portion) of a $P_{2\times7}R$ targeting construct having a sequence that substantially corresponds to, or is substantially complementary to, a predetermined endogenous $P_{2\times7}R$ gene sequence, which can include sequences flanking said $P_{2\times7}R$ gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The specific regions of homology required in the targeting construct depend upon the way in which a $P_{2\times7}R$ gene locus is disrupted. The regions of homology are generally present in a targeting construct in the same 5' to 3' orientation relative to one another. The terms "homology clamp" and "homology region" are interchangeable as used herein. Endogenous $P_{2\times7}R$ gene sequences that substantially correspond to, or are substantially complementary to, a transgene homology region are referred to herein as "crossover target sequences" or "endogenous target sequences."

Homology regions that are isogenic to the target cells generally enhance the efficiency of gene targeting. The polynucleotide sequences that can be used as homology clamps in a targeting construct can be obtained, e.g., from GenBank database, in literature publications, or by routine cloning and sequencing, etc. $P_{2\times7}R$ polynucleotide sequences include, but are not limited to, those polynucleotide sequences found in Genbank Accession No. NM_0011207, Genbank Accession No. NM_002562, and Genbank Accession No. X95882. Typically, a $P_{2\times7}R$ gene sequence is used as a basis for producing PCR primers that flank a region that will be used as a homology clamp in a targeting construct. The PCR primers are then used to amplify, by high fidelity PCR amplification (Mattila et al. (1991) *Nucl. Acids Res.* 19:4967; Eckert and Kunkel (1991) *PCR Methods Appl.* 1:17; and U.S. Pat. No. 4,683,202), a genomic sequence from a genomic clone library or from a preparation of genomic DNA, preferably from the strain of non-human animal that is to be targeted with the targeting construct. The amplified DNA is then used as a homology clamp and/or targeting region. Thus, homology clamps for targeting essentially any $P_{2\times7}R$ gene may be readily produced on the basis of nucleotide sequence information available in the art and/or by routine cloning.

A $P_{2\times7}R$ targeting region is a portion of a $P_{2\times7}R$ targeting construct that becomes integrated into an endogenous $P_{2\times7}R$ chromosomal location following homologous recombination between a homology clamp and an endogenous $P_{2\times7}R$ gene sequence. Typically, a $P_{2\times7}R$ targeting region is flanked on each side by a $P_{2\times7}R$ homology clamp, such that a double-crossover recombination between each of the homology clamps, and their corresponding endogenous $P_{2\times7}R$ gene sequences, results in replacement of the portion of the endogenous $P_{2\times7}R$ gene locus by the targeting region; in such double-crossover gene replacement targeting constructs the targeting region can be referred to as a "$P_{2\times7}R$ replacement region." However, some targeting constructs may employ only a single $P_{2\times7}R$ homology clamp (e.g., some "hit-and-run"-type vectors; see, Bradley et al. (1992) *BioTechnol.* 10:534). Homology regions and targeting regions are linked together in conventional linear polynucleotide linkage (5' to 3' phosphodiester backbone).

A $P_{2\times7}R$ replacement region is a portion of a $P_{2\times7}R$ targeting construct flanked by $P_{2\times7}R$ homology regions. Upon double-crossover homologous recombination between flanking homology regions and their corresponding endogenous $P_{2\times7}R$ gene crossover target sequences, the replacement region is integrated into the host cell chromosome between the endogenous crossover $P_{2\times7}R$ target sequences. Replacement regions can be homologous (e.g., have a sequence similar to the endogenous $P_{2\times7}R$ gene sequence but have a point mutation or a missense mutation), nonhomologous (e.g., a neo gene expression cassette), or a combination of homologous and nonhomologous regions.

Generally, targeting constructs of the invention preferably include: (1) a positive selection expression cassette flanked by two homology regions that are substantially identical to host cell endogenous $P_{2\times7}R$ gene sequences; and (2) a distal negative selection expression cassette. However, targeting constructs which include only a positive selection expression cassette can also be used. Typically, a targeting construct contains a positive selection expression cassette which includes a neo gene under the control of a promoter, such as the HSV tk promoter or the pgk promoter. More typically, the targeting construct will also contain a negative selection expression cassette which includes an HSV tk gene linked downstream of a HSV tk promoter.

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the marker between the homology regions (i.e., the replacement region) into a $P_{2\times7}R$ gene by selecting for the presence of the positive marker and for the absence of the negative marker. Selectable markers typically are also used for hit-and-run targeting constructs and selection schemes (Valancius and Smithies (1991) *Mol. Cell. Biol.* 11: 1402).

Positive-negative selection involves the use of two active selection cassettes: (1) a positive one (e.g., the neo gene) that can be stably expressed following either random integration or homologous targeting, and (2) a negative one (e.g., the HSV tk gene) that is stably expressed following random integration, but not after integration of the construct following correctly targeted double-crossover homologous recombination. By combining both positive and negative selection steps, host cells having the correctly targeted homologous recombination between the transgene and the endogenous $P_{2x7}R$ gene can be obtained.

Other negative selectable markers (and their agents of selection) include Hprt (hypoxanthine), and diphtheria toxin, ricin toxin, or cytosine deaminase (all selected by 5-fluorocytosine). Further examples of positive-negative selection schemes are described, for example, in U.S. Pat. No. 5,464,764 and in WO 94/06908. It is recognized, however, that one or more negative selectable markers are not required in the targeting vector in order to carry out the present invention.

An expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e.g., by hormones such as glucocorticoids; MMTV promoter), but is expressed prior to and/or during selection. An expression cassette can optionally include one or more enhancers, typically linked upstream of the promoter and within about 3–10 kilobases. However, when homologous recombination at the targeted endogenous site(s) places the nonhomologous sequence in the proper reading frame downstream of a functional endogenous promoter, it may be possible for the targeting construct replacement region to comprise only a structural sequence encoding the selectable marker, and rely upon the endogenous promoter to drive transcription (Doetschman et al. (1988) *Proc. Natl. Acad. Sci. (USA)* 85:8583). Similarly, an endogenous enhancer located near the targeted endogenous site may be relied on to enhance transcription of transgene sequences in enhancerless transgene constructs. Preferred expression cassettes of the invention encode and express a selectable drug resistance marker and/or a HSV thymidine kinase enzyme. Suitable drug resistance genes include, for example: gpt (xanthine-guanine phosphoribosyltransferase), which can be selected for with mycophenolic acid; neo (neomycin phosphotransferase), which can be selected for with G418 or hygromycin; and dihydrofolate reductase (DFHR), which can be selected for with methotrexate (Mulligan and Berg (1981) *Proc. Natl. Acad. Sci. (USA)* 78:2072; Southern and Berg (1982) *J. Mol. Appl. Genet.* 1:327; which are incorporated herein by reference).

Selection for correctly targeted recombinants generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it would integrate only by nonhomologous recombination. Such positioning generally is accomplished by lining the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location. A nucleoside analog, gancyclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

Any of a wide variety of cloning vectors may be used to construct the $P_{2x7}R$-targeting constructs of the present invention. Examples of such cloning vectors include, but are not limited to, pBR322 and pBR322-based vectors (Sekiguchi (1983) *Gene* 21:267), pMB9, pBR325, pKH47, pBR328, pHC79, phage Charon 28 (Boehringer Mannheim Biochemicals, Indianapolis, Ind.), pKB11, pKSV-10 (P-L Biochemicals), and oligonucleotide (dg)-tailed pBR322, pBluescript or similar plasmids (Stratagene, La Jolla, Calif.), pK19 or related plasmids (New England Biolabs, Beverly, Mass.), the pUC series of plasmids (New England Biolabs, Beverly, Mass.), the pGEM series of plasmids (Promega, Madison, Wis.), and the like.

The specific host employed for propagating the targeting constructs of the present invention is not critical, but the host will preferably have a functional hsd modification system. Examples of such hosts include *E. coli* K12 RR1 (Bolivar et al. (1977) *Gene* 2:95); *E. coli* K12 HB101 (ATCC No. 33694); *E. coli* MM21 (ATCC No. 336780); and *E. coli* DH1 (ATCC No. 33849). Similarly, alternative vector/cloning systems could be employed such as targeting vectors which grow in *E. coli* or *Saccharomyces cerevisiae*, or both, or plasmid vectors which grow in *B. subtilus* (Ure et al. (1983) *Meth. Enzymol.* 101: Part C).

Targeting constructs propagated in such hosts as *E. coli* are isolated using standard molecular biology methods, or may be synthesized as oligonucleotides. Targeting transgenes can be transferred to host cells by any suitable technique, including microinjection, electroporation, lipofection, biolistics, calcium phosphate precipitation, and viral-based vectors, among others. Other methods used to transform mammalian cells include the use of Polybrene, protoplast fusion, and others (see, generally, Sambrook et al. *Molecular Cloning: A Laboratory Manual*, 2d ed., 1989, Cold Spring Harbor Laboratory Press, Cold Spring Harbor, N.Y.). The preferred method is electroporation.

It is preferable to use a transfection technique with linearized transgenes containing only modified target gene sequence(s) and without vector sequences. The modified gene site is such that a homologous recombinant between the exogenous targeting construct and the endogenous DNA target sequence can be identified by using carefully chosen primers and PCR or by Southern blot analysis, followed by analysis to detect if PCR products or Southern blot bands specific to the desired targeted event are present (Erlich et al. (1991) *Science* 252:1643).

Several studies have already used PCR to successfully identify the desired transfected cell lines (Zimmer and Gruss (1989) *Nature* 338:150; Mouellic et al. (1990) *Proc. Natl. Acad. Sci. (USA)* 87:4712; Shesely et al. (1991) *Proc. Natl. Acad. Sci. (USA)* 88:4294). This approach is very effective when the number of cells receiving exogenous targeting transgene(s) is high (i.e., with electroporation or with liposomes) and the treated cell populations are allowed to expand (Capeechi (1989) *Trends Genet.* 5:70). The targeting construct may be introduced into the germline of an animal cell by methods including, e.g., by pronuclear injection of recombinant genes into pronuclei of one-cell embryos, incorporating an artificial yeast chromosome into embryonic stem cells, gene targeting methods, or embryonic stem cell methodology. See, e.g., U.S. Pat. Nos. 4,736,866; 4,873,191; 4,873,316; 5,082,779; 5,304,489; 5,174,986; 5,175,384; 5,175,385; 5,221,778; Gordon et al. (1980) *Proc. Natl. Acad. Sci. (USA)* 77:7380–7384; Palmiter et al. (1985) *Cell* 41:343–345; Palmiter et al. (1986) *Ann. Rev. Genet.* 20:465–499; Askew et al. (1993) *Mol. Cell. Bio.* 13:4115–4124; Games et al. (1995) *Nature* 373:523–527; Valancius and Smithies (1991) *Mol. Cell. Bio.* 11: 1402–1408; Stacey et al. (1994) *Mol. Cell. Bio.* 14:1009–1016; Hasty et al. (1995) *Nature* 350:243–246; Rubinstein et al. (1993) *Nucl. Acid Res.* 21:2613–2617.

Another method available for inserting a foreign nucleic acid sequence into the $P_{2x7}R$ gene locus to disrupt its expression is gene trapping. This method takes advantage of the cellular machinery present in all mammalian cells that splices exons into mRNA to insert a gene trap vector coding sequence into a gene in a random fashion. Once inserted, the gene trap vector creates a mutation in the trapped gene and disrupts its expression. By contrast to homologous recombination, this system of mutagenesis is largely random. Thus, to obtain a genetically modified cell that contains the desired mutation of a $P_{2x7}R$ gene, this cell is typically selected from a pool of cells that contain mutations in a variety of genes.

Gene trapping systems and vectors have been described for use in genetically modified murine cells and other cell types (see, e.g., Allen et al. (1988) *Nature* 333:852–55; Bellen et al. (1989) *Genes Dev.* 3:1288–1300; Bier et al. (1989) *Genes Dev.* 3:1273–1287; Bonnerot et al. (1992) *J. Virol.* 66:4982–91; Brenner et al. (1989) *Proc. Nat. Acad. Sci. (USA)* 86:5517–21; Friedrich et al. (1993) *Meth. Enzymol.* 225:681–701; Friedrich et al. (1991) *Genes Dev.* 5:1513–23; Goff (1987) *Meth. Enzymol.* 152:469–81; Gossler et al., (1989) *Science* 244:463–65; Hope (1991) *Develop.* 113:399–408; Kerr et al. (1989) *Cold Spring Harb. Symp. Quant. Biol.* 2:767–776; Reddy et al. (1991) *J. Virol.* 65:1507–1515; Reddy et al. (1992) *Proc. Natl. Acad. Sci. (USA)* 89:6721–25; Skarnes et al. (1992) *Genes Dev.* 6:903–918; von Melchner et al. (1989) *J. Virol.* 63:3227–3233; and Yoshida et al. (1995) *Transgen. Res.* 4:277–87).

Promoter trap, or 5', vectors contain, in 5' to 3' order, a splice acceptor sequence followed by an exon typically characterized by a translation initiation codon and open reading frame and/or an internal ribosome entry site. In general, these promoter trap vectors do not contain promoters or operably linked splice donor sequence sequences. Consequently, after integration into the cellular genome of the host cell, the promoter gene trap cassette intercepts the normal splicing of the upstream gene and acts as a terminal exon. Expression of the vector coding sequence is dependent upon the vector integrating into an intron of the disrupted gene in the proper reading frame. In such a case, the cellular splicing machinery splices exons from the trapped gene upstream of the vector coding sequence (Zambrowicz et al., WO 99/50426).

An alternative method for producing an effect similar to the above-described promoter trap vector is a vector that incorporates a nested set of stop codons present in, or otherwise engineered into, the region between the splice acceptor of the promoter trap vector and the translation initiation codon or polyadenylation sequence. The coding sequence can also be engineered to contain an independent ribosome entry site (IRES) so that the coding sequence will be expressed in a manner largely independent of the site of integration within the host cell genome. Typically, but not necessarily, an IRES is not used in conjunction with a nested set of stop codons.

Another type of gene trapping scheme uses a 3' gene trap vector. This type of vector contains, in operative combination, a promoter region that mediates expression of an adjoining coding sequence, the coding sequence, and a splice donor sequence that defines the 3' end of the coding sequence exon. After integration into a host cell genome, the transcript expressed by the vector promoter is spliced to a splice acceptor sequence from the trapped gene that is located downstream of the integrated gene trap cassette. Thus, the integration of the vector results in the expression of a fusion transcript comprising the coding sequence of the 3' gene trap cassette and any downstream cellular exons, including the terminal exon and its polyadenylation signal. When such vectors integrate into a gene, the cellular splicing machinery splices the vector coding sequence upstream of the 3' exons of the trapped gene. One advantage of such vectors is that the expression of the 3' gene trap vectors is driven by a promoter within the gene trap cassette and does not require integration into a gene that is normally expressed in the host cell (Zambrowicz et al., WO 99/50426).

Examples of transcriptional promoters and enhancers that may be incorporated into the 3' gene trap cassette include, but are not limited to, cell or tissue specific promoters, inducible promoters, the herpes simplex thymidine kinase promoter, cytomegalovirus (CMV) promoter/enhancer, SV40 promoters, PGK promoter, regulatable promoters (e.g., metallothioneine promoter), adenovirus late promoter, vaccinia virus 7.5K promoter, avian beta globin promoter, histone promoters (e.g., mouse histone H3-614), beta actin promoter, and the cauliflower mosaic virus 35S promoter (see generally, Sambrook et al., *Molecular Cloning*, Vols. I–III, Cold Spring Harbor Laboratory Press, Cold Spring Harbor, N.Y. (1989), and *Current Protocols in Molecular Biology*, John Wiley & Sons (1989–2000 editions)).

The promoter gene trap or 3' gene trap cassette is introduced into target cells as a structural component of any of a wide range of vectors that can be specifically or nonspecifically inserted into the target cell genome. Suitable vectors that can be used in conjunction with the presently disclosed features include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in *Viral Vectors: Gene Therapy and Neuroscience Applications*, Editors Caplitt and Loewy, Academic Press, San Diego, 1995. Preferably, retroviral vectors are used for gene trapping. These vectors can be used in conjunction with retroviral packaging cell lines such as those described in U.S. Pat. No. 5,449,614. Where non-murine mammalian cells are used as target cells for genetic modification, amphotropic or pantropic packaging cell lines can be used to package suitable vectors (Ory et al. (1996) *Proc. Natl. Acad. Sci. (USA)* 93:11400–11406). Representative retroviral vectors that can be adapted to incorporate the presently described 3' gene trap cassette are described, for example, in U.S. Pat. No. 5,521,076.

The gene trapping cassettes can contain one or more of the heterologous marker genes discussed above with respect to targeting vectors used for homologous recombination. The marker gene may be engineered to contain an independent ribosome entry site (IRES) so that the marker is expressed in a manner largely independent of the location in which the vector has integrated into the target cell genome. Similar to their use in targeting vectors, markers are used in gene trapping vectors to select cells that have integrated the vector into the cell genome.

Of course, gene trap vectors will integrate into the genome of infected host cells in a fairly random manner. Therefore, a genetically modified cell of the present invention which has a disrupted $P_{2x7}R$ gene must be identified from a population of cells that have undergone random vector integration. Preferably, the genetic modifications in the population of cells are of sufficient randomness and frequency such that the population represents mutations in essentially every gene found in the cell's genome, making it likely that a cell with a disrupted $P_{2x7}R$ gene will be identified from the population (see Zambrowicz et al., WO 99/50426; Sands et al., WO 98/14614).

Individual mutant cells containing a disrupted $P_{2x7}R$ gene are identified in the population of mutated cells using, for example, reverse transcription and polymerase chain reaction (PCR) to identify a mutation in a $P_{2x7}R$ gene sequence. This process can be streamlined by pooling clones. For example, to find an individual clone containing a disrupted $P_{2x7}R$ gene, RT-PCR is performed using one primer anchored in the gene trap vector and the other primer located in the $P_{2x7}R$ gene sequence. A positive RT-PCR result indicates that the vector sequence is encoded in the $P_{2x7}R$ gene transcript, indicating that $P_{2x7}R$ gene has been disrupted by a gene trap event (see, e.g., Sands et al., WO 98/14614).

For making non-human genetically modified animals containing one or more disrupted $P_{2x7}R$ genes, embryonic stem cells (ES cells) genetically modified by homologous recombination, gene trapping, or any other method known in the art, are preferred. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435–438; and Schwartzberg et al. (1989) *Science* 246:799–803). Primary isolates of ES cells may be obtained directly from embryos, essentially as described for the EKCCE cell line or for ES cells in general. The particular embryonic stem cell employed in the present invention is not critical. ES cells are preferably cultured on stromal cells, e.g., STO cells and/or primary embryonic fibroblast cells as described by Robertson (1987) in *Teratocarcinomas and Embryonic Stem Cells: a Practical Approach*, E. J. Robertson, ed. (Oxford: IRL Press), pp. 71–112. The stromal (and/or fibroblast) cells serve to reduce the clonal outgrowth of abnormal ES cells.

The present invention encompasses ES cells transfected with a targeting construct and their progeny or potential progeny. While the ES cells of the invention are homozygous or heterozygous for the $P_{2x7}R$ disruption, they may not be identical to the parent ES cell transfected with the targeting construct due to mutations or environmental influences that may occur in other genes in succeeding generations.

Where the non-human genetically modified animal is a mouse, murine ES cells are used, such as AB-1 line grown on mitotically inactive SNL76/7 cell feeder layers (McMahon and Bradley (1990) *Cell* 62:1073–1085). Other suitable ES lines include, but are not limited to, the E14 line (Hooper et al. (1987) *Nature* 326: 292–295), the D3 line (Doetschman et al. (1985) *J. Embryol. Exp. Morph.* 87:27–45), and the CCE line (Robertson et al. (1986) *Nature* 323:445–448), the RW4 cell line (available from Genome Sciences), and the DBA cell line (Roach et al. (1995) *Exp. Cell Res.* 221:520–525).

The $P_{2x7}R$ targeting transgene is transferred into mouse ES cells (e.g., by electroporation) under conditions suitable for the continued viability of the electroporated ES cells. The electroporated ES cells are cultured under selective conditions for positive selection (e.g., a selective concentration of G418), and optionally are cultured under selective conditions for negative selection (e.g., a selective concentration of gancyclovir or FHAU), either simultaneously or sequentially. Selected cells are then verified as having the correctly targeted transgene recombination by PCR analysis according to standard PCR or Southern blotting methods known in the art (see, e.g., U.S. Pat. No. 4,683,202; and Erlich et al. (1991) *Science* 252:1643). Correctly targeted ES cells are then transferred into suitable blastocyst hosts for generation of chimeric genetically modified animals according to methods known in the art (Capecchi (1989) *Trends Genet.* 5:70). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The ES cells bearing a specific targeted mutation are injected into mouse blastocysts as described by Bradley, 1987, in *Teratocarcinomas and Embryonic Stem Cells: A Practical Approach*, E. Robertson, ed. (Oxford: IRL Press), pp. 113–151. The particular mouse blastocysts employed in the present invention are not critical. Examples of such blastocysts include those derived from C57BLU6 mice, C57BL/6 Albino, Swiss outbred, CFLP, MFI, and the like. The blastocysts containing the injected ES cells are allowed to develop in the uteri of pseudopregnant non-human female mice and are born as chimeric mice. Chimeric targeted mice are derived according to Hogan et al., *Manipulating the Mouse Embryo: A Laboratory Manual*, Cold Spring Harbor Laboratory, 1988; and *Teratocarcinomas and Embryonic Stem Cells: A Practical Approach*, E. J. Robertson, ed., IRL Press, Washington, D.C., 1987. The resultant genetically modified mice are chimeric for cells having an inactivated endogenous $P_{2x7}R$ loci and are backcrossed and screened for the presence of the correctly targeted transgene(s) by PCR or Southern blot analysis on tail biopsy DNA of offspring so as to identify genetically modified mice heterozygous for the inactivated $P_{2x7}R$ locus/loci. By performing the appropriate crosses, it is possible to produce a genetically modified non-mouse homozygous for a disrupted $P_{2x7}R$ locus ($P_{2x7}R^{-/-}$) $P_{2x7}R^{-/-}$ genetically modified mice may also be crossed to mice carrying other mutations, such as $P_{2x1}R^{-/-}$ mice.

In certain embodiments of the present invention, a disruption in the endogenous $P_{2x7}R$ gene locus in non-human genetically modified animals is limited to specific developmental stages or to specific tissues. In other embodiments, a disruption in the endogenous $P_{2x7}R$ gene locus in non-human genetically modified animals or cells derived from the non-human genetically modified animals is inducible.

Where the disruption in the $P_{2x7}R$ gene locus is desired to be temporally or developmentally regulated, the Cre-Lox system may be employed. The Cre-Lox system may be used to activate or inactivate the $P_{2x7}R$ gene at a specific developmental stage or in a particular tissue. Generally, methods utilizing Cre-Lox technology are carried out as described by Torres and Kuhn (1997) *Laboratory Protocols for Conditional Gene Targeting*, Oxford University Press. Methodology similar to that described for the Cre-Lox system can be employed utilizing the FLP-FRT system.

For inactivation of endogenous $P_{2x7}R$ gene expression at a specific stage in development or a particular tissue, the $P_{2x7}R$ coding region is replaced by a cassette comprising the coding region flanked by LoxP cites according to the methods described herein. The LoxP sites are targets for the Cre recombinase. The resulting genetically modified animal is crossed to another genetically modified animal in which the Cre recombinase is expressed under the control of a spatially and/or temporally regulated promoter. When Cre expression is activated, the LoxP sites undergo recombination to excise the endogenous $P_{2x7}R$ coding region, resulting in $P_{2x7}R$-deficient tissues.

For activation of endogenous $P_{2x7}R$ gene expression in a selected tissue and or at a particular stage of development, the regions of homology in the targeting construct are promoter sequences, comprising an insertion fragment which contains multiple stop codons in all reading frames flanked by LoxP sites. Upon insertion of this targeting construct into the $P_{2x7}R$ promoter, no $P_{2x7}R$ protein is produced. The resulting genetically modified animal is crossed to another genetically modified animal in which the Cre recombinase is expressed under the control of a spatially and/or temporally regulated promoter. When Cre expression is activated, the LoxP sites undergo recombination to excise the stop codons and restore the $P_{2x7}R$ gene to its undisrupted state.

For inducible $P_{2x7}R$ activation or inactivation, the Tet operator is inserted into the endogenous $P_{2x7}R$ regulatory elements, so that the $P_{2x7}R$ gene falls under the control of the tetracycline-controllable transactivator (tTA) and tetracycline-controllable repressor (TetR), which can only activate or repress transcription, respectively, in the presence of tetracycline. Genetically modified animals comprising the Tet promoter in the $P_{2x7}R$ gene are then crossed to animals which express rTA or TetR, constitutively for example, and $P_{2x7}R$ expression is induced or repressed by administering tetracycline to the animals. Alternatively, cultured cells from the genetically modified animals can be produced, the cells transfected with a rTA or TetR expression construct, and the culture contacted with tetracycline to induce or inhibit $P_{2x7}R$ expression. For further details, see U.S. Pat. No. 5,922,927.

The extent of $P_{2x7}R$ deficiency resulting in a disruption in the endogenous $P_{2x7}R$ gene loci or locus in non-human genetically modified animals and cells derived therefrom can easily be measured by using standard molecular biology methods. For instance, one can measure for a deficiency in $P_{2x7}R$ messenger RNA levels by using reverse transcriptase mediated polymerase chain reaction (RT-PCR), Northern blot analysis, or in situ hybridization.

In other embodiments, the extent of $P_{2x7}R$ deficiency resulting from a disruption in the endogenous $P_{2x7}R$ gene loci or locus in a non-human genetically modified animal of the invention can be assayed by measuring protein levels or activity by various methods. For example, in one embodiment, protein extracts from cells having a disruption in the endogenous $P_{2x7}R$ gene loci or locus-deficient cells and tissues are assayed for their levels of $P_{2x7}R$ protein by affinity to various immunoassays known in the art. Such immunoassays include but are not limited to competitive and non-competitive assay systems using techniques such as radioimmunoassays (RIA), enzyme linked immunosorbent assay (ELISA), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, immunofluorescence assays, protein A assays, and immunoelectrophoresis assays, etc. In one mode of the embodiment, antibody binding is detected by detecting a label on the primary antibody. In another mode of embodiment, the primary antibody is detected by detecting binding of a secondary antibody or reagent to the primary antibody. Optionally, the secondary antibody can be labeled. Many means are known in the art for detecting binding in an immunoassay and are within the scope of the present invention.

Methods of measuring the $P_{2x7}R$-like activities are described herein in the Example below and in the literature. Examples of such methods are as follows: ATP-induced changes in cell permeability can be measured by cellular electrophysiological changes and/or the cellular accumulation of macromolecules such as dyes (see, e.g., Michel et al. (1998) Br. J. Pharmacol. 124:1194–1201; Virginio et al. (1999) J. Physiol. 519:335–346; and the Examples disclosed herein); changes in ATP-induced posttranslational processing and production of interleukins can be measured using immunoprecipitation and/or ELISA assays (e.g., as further described in the Example below); and changes in lymphoproliferation can be measured as reported in Baricordi et al. (J. Biol. Chem. (1999) 274:33206–33208).

Techniques known to those of skill in the art can be used to measure cell proliferation. For example, cell proliferation can be measured by counting samples of a cell population over time (e.g. daily cell counts). Cells can be counted using a hemacytometer and light microscopy (e.g., HyLite hemacytometer, Hausser Scientific). Cell number can be plotted against time in order to obtain a growth curve for the population of interest. In a preferred embodiment, cells counted by this method are first mixed with the dye Trypanblue (Sigma, St. Louis, Mo.), such that living cells exclude the dye, and are counted as viable members of the population. Cell proliferation can also be measured using ($^3$H)-thymidine incorporation (see, e.g., Chen (1996) Oncogene 13:1395–403; Jeoung (1995) J. Biol. Chem. 270:18367–73). This assay allows for quantitative characterization of S-phase DNA synthesis. In this assay, cells synthesizing DNA incorporate ($^3$H)-thymidine into newly synthesized DNA. Incorporation can then be measured by standard techniques in the art such as by counting of radioisotope in a Scintillation counter (e.g., Beckman LS 3800 Liquid Scintillation Counter).

The cells from a non-human genetically modified animal can be isolated from tissue or organs using techniques known to those of skill in the art. For example, immune cells can be collected or isolated from blood, or secondary lymphoid organs of the subject such as, but not limited to, lymph nodes, tonsils, the spleen, Peyer's patch of the intestine, and bone marrow, by any of the methods known in the art (see, e.g., Current Protocols in Immunology (1991) Green Publishing Associates, New York, N.Y., p. 21). Immune cells obtained from such sources typically comprise predominantly recirculating lymphocytes and macrophages at various stages of differentiation and maturation. Optionally, standard techniques, such as morphological observation and immunochemical staining, can be used, if desired, to verify the presence of the desired cells, e.g., dendritic, T cells, and macrophages. The immune cells used in the in vitro methods of the invention can be collected by standard techniques, such as by use of a syringe to withdraw the blood, followed by subjecting the blood to Ficoll-Hypaque (Pharmacia) gradient centrifugation. Blood, anticoagulated with preservative-free heparin, usually yields $0.5–1.0 \times 10^6$ lymphocytes/mn. Separated blood cells (e.g., macrophages) may be frozen by standard techniques prior to use in the present methods. In a specific embodiment, the immune cells used are purified white blood cells comprising lymphocytes and macrophages.

Monocyte-derived macrophages can be isolated from immune cells by allowing the cells to adhere to culture flasks for 1–2 hours, washing away nonadherent cell and culturing adherent cells for 7–12 days in medium (i.e., RMPI 1640 supplemented with 20% human serum, 2 mM glutamine, 5 mM HEPES, and 100 μg/ml streptomycin) plus interferon-γ (IFN-γ). See, e.g., Blanchard et al. (1995) J. Cell. Biochem. 57:452–464; and Blanchard et al. (1991) J. Immunol. 147:2579–2585.

In one embodiment, antibodies against specific surface markers can be directly labeled by conjugation of an affinity compound to such antibodies to facilitate detection and separation of macrophages or lymphocytes. Alternatively, in another embodiment, the primary antibody is detected by detecting binding of a secondary antibody or reagent to the primary antibody. In a further embodiment, the secondary antibody is labeled.

Affinity compounds that can be used include, but are not limited to, biotin, photobiotin, fluorescein isothiocyanate (FITC), or phycoerythrin (PE), or other compounds known in the art. Cells retaining labeled antibodies are then separated from cells that do not bind such antibodies by techniques known in the art such as, but not limited to, various cell sorting methods (e.g., fluorescence activated cell sorter (FACS) or magnetic activated cell sorting (MACS), affinity chromatography, and panning).

In one embodiment, cells isolated from a non-human genetically modified animal of the invention are immortalized. In accordance with this embodiment, cells derived from the non-human genetically modified animal can be immortalized by genetically engineering the telomerase gene, an oncogene, e.g., mos or v-src, or an apoptosis-inhibiting gene, e.g., bcl-2, into the cells. Alternatively, cells derived from the non-human genetically modified animal can be immortalized by fusion with a hybridization partner utilizing techniques known to one of skill in the art.

The present invention encompasses cells isolated from a non-human, genetically modified animal and their progeny or potential progeny. Progeny may not be identical to the parent cells isolated from the non-human, genetically modified animal due to mutations or environmental influences that may occur in succeeding generations.

The present invention encompasses the identification of genes whose expression is upregulated in $P_{2x7}R^{-/+}$ or $P_{2x7}R^{-/-}$ non-human mammals or animal cells relative to their respective control. Techniques known to those of skill in the art can be used to identify such genes. For example, DNA assays can be used to identify genes whose expression is upregulated in $P_{2x7}R^{-/+}$ or $P_{2x7}R^{-/-}$ mice to compensate for a deficiency in $P_{2x7}R$ expression. DNA arrays are known to those of skill in the art. See, e.g., U.S. Pat. No. 5,965,352; Schena et al. (1995) *Science* 270:467–470; DeRisi et al. (1996) *Nature Genetics* 14:457–460; Shalon et al. (1996) *Genome Res.* 6:639–645; and Schena et al. (1995) *Proc. Natl. Acad. Sci. (USA)* 93:10539–11286.

In another application, the genetically-modified $P_{2x7}R^{-/-}$ non-human mammals and animal cells of the invention can be used to determine whether the $P_{2x7}R$ plays a role in causing symptoms to develop in certain models of disease, such as inflammatory diseases and neurodegenerative diseases. For example, if a symptom of inflammation or neurodegeneration is reduced or absent in a $P_{2x7}R^{-/-}$ non-human mammal or animal cell under conditions that induce such a symptom in a corresponding $P_{2x7}R^{+/+}$ or $P_{2x7}R^{+/-}$ non-human mammal or animal cell, then the $P_{2x7}R$ plays a role in curbing the symptoms. Inflammation can be assessed in wild type mice, $P_{2x7}R^{+/-}$ mice, and $P_{2x7}R^{-/-}$ mice following the onset of arthritis induced, e.g., by administering collagen or collagen fragments (Joosten et al. (1999) *J. Immunol.* 163:5049–55), by administering collagen monoclonal antibodies (Terato et al. (1992) *J. Immunol.* 148:2103–08), or by administering zymosan (Van de Loo et al. (1995) *Arthritis Rheuma.* 38:164–72). The inflammation can be detected using any method known to those of skill in the art. For example, inflammation can be detected histologically by computed tomography (CT), magnetic resonance imaging (MRI), ultrasonography, scintigraphic imaging, or by visual observation of symptoms such as swelling or redness.

Such comparison can also be made in models of neurodegeneration. Alzheimer's disease can be induced in a mouse, for example, by expressing human familial Alzheimer's disease (FAD) β-amyloid precursor (APP) in the mouse, overexpressing human wild-type APP in the mouse, overexpressing β-amyloid 1-42 (βA) in the mouse, or expressing FAD presenillin-1 (PS-1) in the mouse. (See, e.g., Higgins (1999) *Mol. Med. Today* 5:274–276.) Gene products with altered concentrations in genetically modified mice with Alzheimer's disease which can be measured include, but are not limited to, amyloid β-peptides (Aβ), tau protein, and neuronal thread protein (NTP) in the CSF of the mouse. Stroke can be induced in mouse, for example, by middle cartoid artery occlusion (see, e.g., Garcia et al. (1995) *Am. J. Pathol.* 147:1477–86; Hara et al. (1997) *Proc. Natl. Acad. Sci. (USA)* 94:2007–12).

Under circumstances in which an agent has been identified as a $P_{2x7}R$ agonist or antagonist (e.g., the agent significantly modifies one or more of the $P_{2x7}R$ polypeptide activities described herein when the agent is administered to a $P_{2x7}R^{+/+}$ or $P_{2x7}R^{+/-}$ non-human mammal or animal cell), the genetically-modified, $P_{2x7}R^{-/-}$ animal cells of the invention are useful to characterize any other effects caused by the agent besides those known to result from the (ant)agonism of a $P_{2x7}R$. For example, if the administration of the agent causes an effect in a $P_{2x7}R^{+/+}$ non-human mammal or animal cell that is not known to be associated with $P_{2x7}R$ polypeptide activity, then one can determine whether the agent exerts this other effect solely or primarily through modulation of the $P_{2x7}R$ by administering the agent to a corresponding $P_{2x7}R^{-/-}$ non-human mammal or animal cell. If this other effect is absent, or is significantly reduced, in the $P_{2x7}R^{-/-}$ non-human mammal or animal cell, then the other effect is mediated, or at least in part, by the $P_{2x7}R$. However, if the $P_{2x7}R^{-/-}$ non-human mammal or animal cell exhibits the other effect to a degree comparable to the $P_{2x7}R^{+/+}$ or $P_{2x7}R^{+/-}$ non-human mammal or animal cell, then the other effect is mediated by a pathway that does not involve $P_{2x7}R$ 20 signaling.

Examples of agents that may be identified as $P_{2x7}R$ antagonists or agonists include, but are not limited to, nucleic acids (e.g., DNA and RNA), carbohydrates, lipids, proteins, peptides, peptidomnimetics, small molecules, and other drugs that modulate a $P_{2x7}R$-like activity in an animal cell. Such agents may be identified from libraries of agents that are obtained using any methods such as the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (e.g., Lam (1997) *Anticancer Drug Des.* 12:145; U.S. Pat. No. 5,738,996; and U.S. Pat. No. 5,807,683).

Examples of methods for the synthesis of molecular libraries can be found in the art, for example in: DeWitt et al. (1993) *Proc. Natl. Acad. Sci. (USA)* 90:6909; Erb et al. (1994) *Proc. Natl. Acad. Sci. (USA)* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of agents may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. (USA)* 89:1865–1869) or phage (Scott and Smith (1990) *Science* 249:386–390; Devlin (1990) *Science* 249:404–406; Cwirla et al. (1990) *Proc. Natl. Acad. Sci. (USA)* 87:6378–6382; and Felici (1991) *J. Mol. Biol.* 222:301–310).

Agents that modulate $P_{2x7}R$ activity can be used to treat, inhibit, or prevent certain diseases and disorders associated with aberrant $P_{2x7}R$ expression or activity. Such diseases and disorders include, but are not limited to, glomerular diseases, chronic inflammatory diseases (e.g., arthritis, including rheumatoid arthritis and osteoarthritis, bacterial infection, psoriasis, septicemia, cerebral malaria, inflammatory bowel disease, gastroenteritis, glomerular nephritis, asthma, allergic rhinitis, contact dermatitis, and toxic shock), and neurodegenerative disorders (e.g., Alzheimer's disease, dementia, Parkinson's disease, stroke, Huntington's disease, multiple sclerosis, multiple pontine myelinolysis, human immunodeficiency associated myelopathy, and transverse myelopathy).

EXAMPLES

The following examples are provided for illustrative purposes only and are not to be construed as limiting the present invention in any manner.

I. MATERIALS AND METHODS

Construction of the $P_{2x7}R$ Targeting Vector and Generation of the Knockout Mice A cDNA probe specific for the mouse $P_{2x7}R$ gene was prepared by reverse transcription and PCR amplification using oligonucleotide primers $P_{2x7}R$-F1 (5' CGG CGT GCG TTT TGA CAT CCT 3'; SEQ ID NO: 1) and $P_{2x7}R$-R2 (5' AGG GCC CTG CGG TTC TC 3'; SEQ ID NO:2) which were designed based on the published sequence of the rat sequence of the $P_{2x7}R$ gene (Surprenant et al. (1996) *Science* 272:735–738). Total RNA isolated from the J774 A 1 mouse monocyte/macrophage cell line (American Type Culture Collection, Manassas, Va.) was used as the template RNA. This PCR product was 401 bp long and was cloned and sequenced to verify that it corresponded to the mouse $P_{2x7}R$ gene. The probe was used to screen a 129/Sv mouse genomic library (Stratagene, La Jolla, Calif.), and to isolate a single positive genomic clone. Sequence analysis of BamHI subcloned fragment confirmed that this clone corresponded to the mouse $P_{2x7}R$ gene. A targeting vector was constructed which inserted the neomycin resistance gene from the pJNS2 plasmid (Dombrowicz et al. (1993) *Cell* 75:969–76) directly after the $Arg^{505}$ codon deleting $Cys^{506}$-$Pro^{532}$ in the carboxy region of the $P_{2x7}R$ gene, based on the published sequence (Chessell et al. (1998) *FEBS Lett.* 4390:260–300). The upstream and downstream regions of homology were each approximately 5–8 Kb in length (FIG. 1). One of these two fragments corresponding to the region of the $P_{2x7}R$ gene immediately 5' of the $Arg^{505}$ and the second DNA fragment corresponding to the DNA located 3' of codon $Pro^{532}$ were cloned on either side of the neo gene present in the JNS2 plasmid. These fragments direct the homologous integration of the targeting vector with the endogenous $P_{2x7}R$ gene in the embryonic stem cell line E14TG2a (Hooper et al. (1987) *Nature* 326:292–5). 129/Ola derived E14Tg2a embryonic stem (ES) cells (American Type Culture Collection, Manassas, Va.) (Hooper et al. (1987) *Nature* 326:292–5) were grown, transformed and screened using standard methods (Mohn et al. In: *DNA Cloning* 4, pp. 143–184, Oxford Press, New York, (1995)). Homologous recombination events between the vector and ES cells and genotyping of mice was detected using a probe which hybridizes to a 16 Kb band of the wild type $P_{2x7}R$ locus and a 10 Kb band in the targeted locus (FIG. 2A). This probe was derived from the genomic DNA fragment isolated from the 129/SV library using the $P_{2x7}R$-specific probe. This fragment of DNA corresponds to the region of the $P_{2x7}R$ gene just 5' of the region of the gene used in the construction of the targeting vector. This probe detects a 16 Kb fragment in the wild type and 10 Kb DNA fragment from the targeted allele. Chimeric mice derived from targeted ES cells were mated with B6D2 (C57BL/6×DBA/2F1) or C57BL/6 mice (Jackson Laboratory, Bar Harbor, Me.) to produce heterozygous animals which were then bred to produce homozygous mutant animals. Analysis of RNA prepared from cultured bone marrow derived mast cells from $P_{2x7}R^{+/+}$ and $P_{2x7}R^{-/-}$ mice with $P_{2x7}R$ specific probes verified the loss of expression in $P_{2x7}R^{-/-}$ mice (FIG. 2B).

Peritoneal Macrophage Isolation

Peritoneal macrophages were harvested by injecting 5 ml of Roswell Park Memorial Institute (RPMI) medium containing 5% FBS into each peritoneal cavity, immediately prior to injection, the animals were sacrificed by cervical dislocation. The injected medium was dispersed throughout the peritoneal cavity by rubbing the external surface, after which a hole in the skin covering the peritoneum was made to gain access to the cavity and the injected fluid was recovered with the aid of a transfer pipet. Lavage fluids from multiple animals were pooled and the cells were collected by centrifugation (300×g). These cell pellets were washed twice by centrifugation in RPMI containing 5% fetal calf serum (FCS). A cell count was performed before the final wash.

Western Analysis

Peritoneal macrophage cell pellets were washed once in Cavitation Buffer (25 mM Hepes, pH 7, 30 mM NaCl, 1 mM EDTA, 1 mM dithiothreitol, 1 ug/ml leupeptin, and 1 $\mu$g/ml pepstatin) by centrifugation. Cell pellets then were suspended in 2.5 ml of Cavitation Buffer and the cells were disrupted by nitrogen cavitation (15 minutes on ice at 750 psi). The resulting cell lysates were adjusted to 0.1% saponin, incubated on ice for 30 minutes, and cell membranes subsequently were recovered by centrifugation (50,000 rpm for 30 minutes at 4° C. in a Beckman Ti70 rotor). The membrane pellet was suspended in 2 ml Cavitation Buffer with the aid of a glass tube-teflon pestle homogenizer, and an aliquot or the suspension was set aside for analysis of total protein (Pierce Assay; Pierce, Rockford, Ill.). The membranes again were collected by centrifugation after which the pellets were suspended in 100 $\mu$of 2× Laemmli sample buffer.

Forty mg of protein was loaded into wells of a 4–20% Tris-Glycine gel (Novex, San Diego, Calif.), and, after separation of the proteins, they were transferred to nitrocellulose. These blots were blocked overnight at 4° C. in 1× Western Blocking Reagent (Boehringer Mannheim, Indianapolis, Ind.) in TBS-T (10 mM Tris, pH 8, 150 mM NaCl, 0.1% Tween-20). Blots then were incubated for 2 hours at room temperature in a TBS-T solution containing a 1 to 200 dilution of anti-$P_{2x7}R$ serum (Alomone, Jerusalem, Israel) and 1× Western Blocking Reagent. Blots were washed in TBS-T (two rinses, 15 minutes each), and then incubated for 1 hour with TBS-T containing a 1 to 2000 dilution of horseradish peroxidase-(HRP-)conjugated anti-rabbit IgG-(NE BioLabs; Beverly, Mass.) and 1× Western Blocking Reagent. Blots were washed in TBS-T (two rinses, 15 min each), and then developed with Super Signal (Pierce, Rockford, Ill.) and imaged with a Lumi-Imager (Boehringer Mannheim).

YoPro Yellow Uptake

Peritoneal macrophages were washed with Isotonic Medium (15 mM Hepes, pH 7.2, 135 mM NaCl, 5 mM KCl, 18 mM $CaCl_2$, 08 mM $MgCl_2$) by centrifugation and the resulting cell pellet was suspended in Isotonic Medium to achieve a final cell concentration of 1×10$^6$ cells/ml. Fifty $\mu$l of this cell suspension then was placed into wells of a Microfluor "B" U-bottom plate (Dynatech, Chantilly, Va.), and 50 $\mu$l of 2 $\mu$M YoPro Yellow (Molecular Probes, Eugene, Ore.); the fluorescent dye was dissolved in Isotonic Medium. Wells were then adjusted to 5 mM ATP or 0.0075% saponin by addition of concentrated stock solutions of these agents. Fluorescence was monitored as a function of time at 37° C., excitation, 450 nm/emission, 530 nm.

Stimulus-Induced IL-1β Posttranslational Processing In Vitro

Macrophages from wild type and $P_{2\times7}{}^{-/-}$ animals ($1\times10^6$ cells seeded per well of 6-well cluster plates) were stimulated with 1 μg/ml E. coli LPS (Serotype 055 B5 obtained from Sigma; St. Louis, Mo.) for 75–90 minutes and then rinsed with 2 ml of methionine-free RPMI medium containing 100 units/mi penicillin, 100 μg/ml streptomycin, 1% dialyzed FBS, 1 μg/ml LPS, and 25 mM Hepes, pH 7.3 (Pulse Medium). One ml of Pulse Medium containing 83 μCi/Ml of $^{35}$S-methionine (Amersham Corp, Chicago, Ill.) then was added to each well, and the cells were labeled at 37° C. for 1 hour. These labeled cells subsequently were rinsed twice with RPMI 1640 medium containing 100 units/mil penicillin, 100 μg/ml streptomycin, 1% FBS, 2 mM glutamine, 1 μg/ml LPS and 25 mM Hepes, pH 7.3 (Chase Medium). One ml of Chase Medium (containing no effector (control) or containing 05 mM ATP, or 20 mM nigericin) was then added to each well, and the cells were chased at 37° C. for 30 minutes. Media were harvested and clarified by centrifugation (6000×g for 5 minutes) to remove cells and/or cell debris. Cell monolayers were suspended in 1 ml of a lysis buffer composed of 1% Triton X-100, 150 mM NaCl, 25 mM Hepes, pH 7, 0.1 mM PMSF, 1 mg/ml ovalbumin, 1 mM iodoacetic acid, 1 μg/ml pepstatin, and 1 μg/ml leupeptin. Clarified media samples were adjusted to the same final Triton X-100 and protease inhibitor concentrations by addition of aliquots from concentrated stocks of these reagents. After a 30 minute incubation on ice, all samples were clarified by centrifugation at 45,000 rpm for 30 minutes in a TLA-45 rotor (Beckman, Palo Alto, Calif.), the resulting supernatants were recovered, and IL-1β was immunoprecipitated from these samples using a goat anti-murine IL-1β serum obtained from Dr. Ivan Otterness (Pfizer Central Research, Groton, Conn.). Immnunoprecipitates were fractionated by SDS gel electrophoresis, the quantity of radioactivity associated with individual IL-1β polypeptide species was determined by scanning dried gels with a Phosphoimager.

ATP-Induced IL-1β Posttranslational Processing In Vivo

Groups of mice were injected intraperitoneally (ip) with 1 μg of LPS. Two hours after this LPS injection, mice were injected ip with either 30 mM ATP (adjusted to pH 7) or PBS. Mice were sacrificed 30 minutes or 120 minutes after the ATP or PBS injection and peritoneal cavities were lavaged, each with 3 ml of RPMI (5% FCS). Samples of peritoneal lavages were spun down, supernatants were collected and tested for the presence of IL-1β and IL-6 using ELISAs (Amersham Life Sciences, Arlington Heights, Va. and Endogen, Woburn, Mass., respectively).

II. RESULTS

Generation and Characterization of $P_{2\times7}R^{-/-}$ Mice

Mouse ES cells in which the $P_{2\times7}R$ gene was disrupted by homologous recombination were generated using the scheme shown in FIG. 1. The targeting vector was constructed such that the neomycin-resistance gene was inserted into an exon encoding the carboxy terminus of the wild-type polypeptide. Integration of the targeting vector into the mouse genome by homologous recombination results in replacement of the region of the gene encoding Cys$^{506}$ to Pro$^{532}$ with the neomycin resistance gene. ES cells containing the mutant $P_{2\times7}R$ allele were identified by Southern blot analysis and used to generate the $P_{2\times7}R^{\Delta506-532}$ mouse line. Targeted ES cells contributed to the germline of chimeric mice, and F1 generation$^{+/-}$ animals appeared normal. Homozygous null animals were recovered in the F2 generation with the expected Medelian frequencies. Southern blot analysis of $^{+/-}$ and $^{+/+}$ animals confirmed the success of the targeting strategy. The wild-type and knockout alleles appeared as a 16 kbp and 10 kbp restriction fragments, respectively, on Southern blots (FIG. 2A). Heterozygous ($^{+/-}$) animals demonstrated the presence of both alleles, but the knockouts contained only the targeted allele (FIG. 2A). Northern analysis of RNA isolated from cultured bone marrow mast cells signified that the transcript for the $P_{2\times7}R$ was present in the wild-type ($^{+/+}$) but not knockout ($^{-/-}$) animals (FIG. 2B). $P_{2\times7}R$ knockout animals were viable and fertile, and demonstrated no gross abnormalities.

Figure 3:
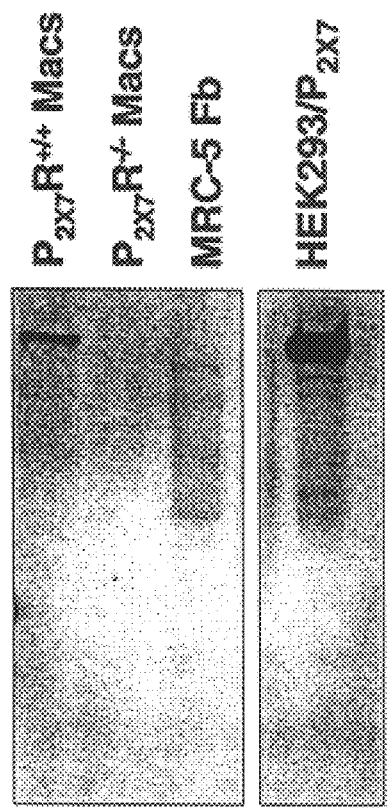
FIG. 3 is a representation of a Western blot showing the absence of $P_{2\times7}R$ protein in the $P_{2\times7}R^{-/-}$ macrophages. Lysates from peritoneal macrophages of $P_{2\times7}R^{-/-}$ mice were tested for expression of $P_{2\times7}R$ by Western Blot analysis: lane 1, $P_{2\times7}R^{+/+}$ macrophages; lane 2, $P_{2\times7}R^{-/-}$ macrophages; lane 3, MRC-5 Fb (negative control); lane 4, $P_{2\times7}R$ expressing HEK293 (positive control)

To demonstrate that the knockout animals lacked the $P_{2\times7}$ receptor ($P_{2\times7}R$), membranes from peritoneal macrophages were compared by Western analysis for the presence of the receptor polypeptide. Membranes from wild-type peritoneal macrophages contained a 76 kDa polypeptide that cross reacted with the $P_{2\times7}R$ antiserum. The size of the murine polypeptide is comparable to that displayed by the human $P_{2\times7}R$ when over expressed in HEK293 cells (FIG. 3). In contrast, macrophage membranes prepared from cells isolated from the knockout animals did not contain a similarly sized polypeptide (FIG. 3).

Figure 4A:
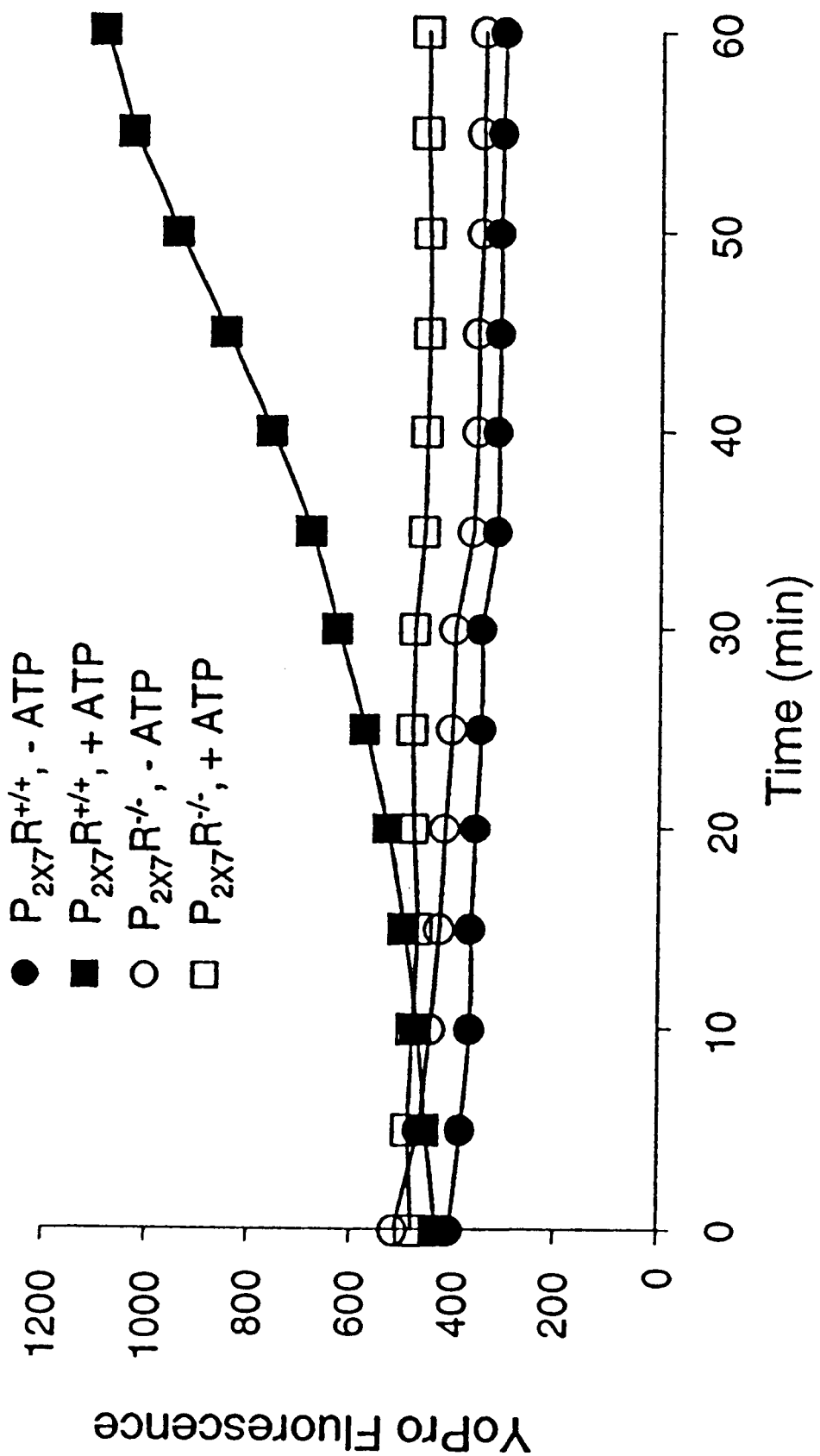
FIG. 4A is a graphic representation of the accumulation of YoPro Yellow in $P_{2\times7}R^{+/+}$ and $P_{2\times7}R^{-/-}$ macrophages in response to ATP stimulation. Peritoneal macrophages isolated from $P_{2\times7}R^{+/+}$ and $P_{2\times7}R^{-/-}$ mice were treated with 5 mM ATP in the presence of YoPro Yellow and fluorescence was measured using a microtiter plate reader.
Figure 4B:
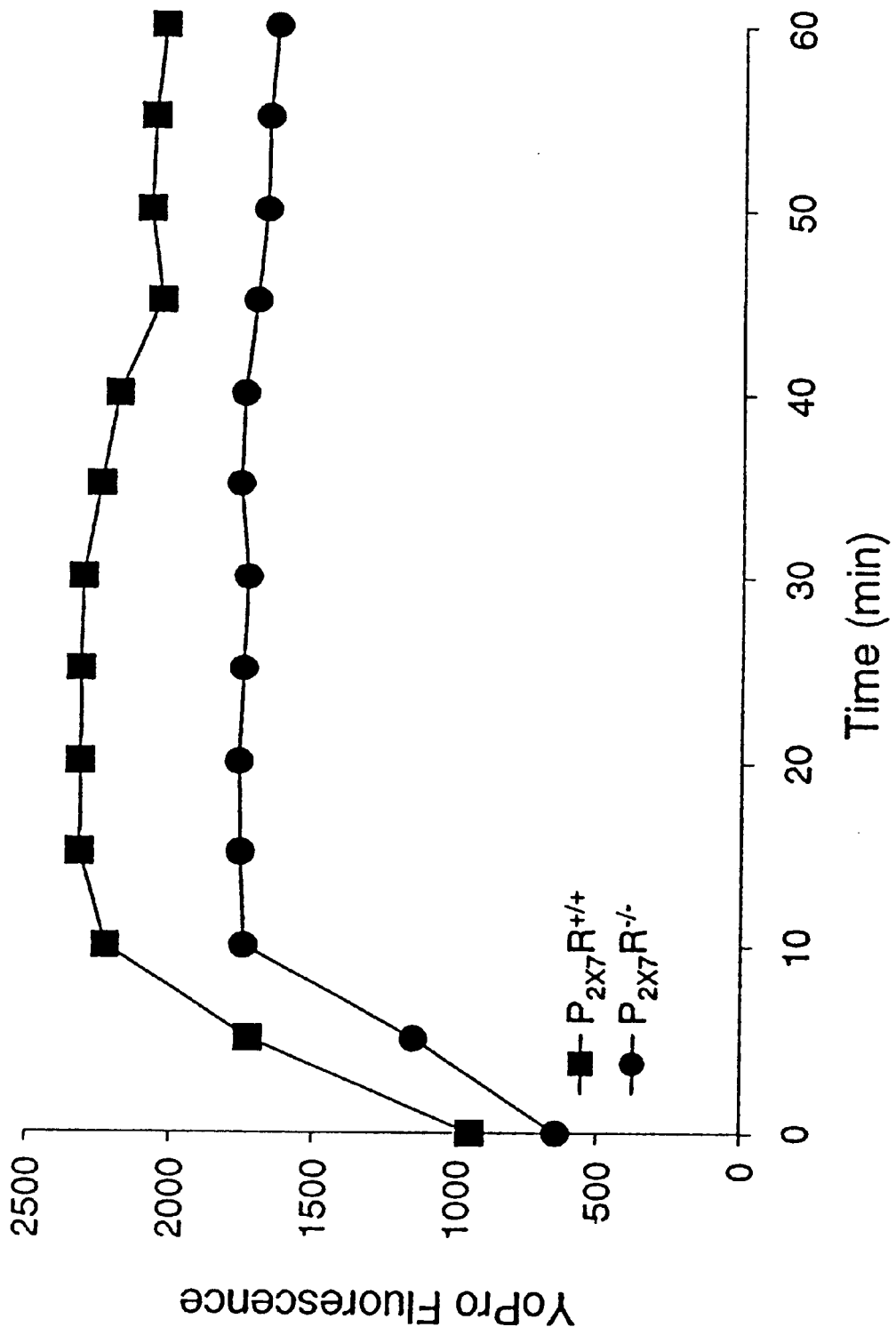
FIG. 4B is a graphic representation of the accumulation of YoPro Yellow in $P_{2\times7}R^{+/+}$ and $P_{2\times7}R^{-/-}$ mice in response to saponin. Peritoneal macrophages isolated from $P_{2\times7}R^{+/+}$ and $P_{2\times7}R^{-/-}$ mice were treated with 0.0075% saponin in the presence of YoPro Yellow and fluorescence was measured using a microtiter plate reader.

A hallmark of the $P_{2\times7}R$ is its ability to facilitate translocation of large organic molecules such as the flourescent dye YoPro Yellow in response to ATP activation (Virginio at al. (1999) J. Physiol. 519:335–346). When mouse peritoneal macrophages isolated from wild-type animals were activated with 5 mM ATP in the presence of extracellular YoPro Yellow, a time dependent increase in fluorescence intensity was observed (FIG. 4). This increase in fluorescence results from internalization of the dye molecules followed by their binding to DNA; when bound to DNA, the fluorescence intensity increases. In the absence of ATP, no significant increase in fluorescence intensity was observed, indicating that YoPro Yellow is impermeant to the plasma membrane in the absence of the nucleotide triphosphate. In contrast, addition of ATP to macrophages isolated from $P_{2\times7}R^{-/-}$ mice did not result in time-dependent increase in fluorescence intensity (FIG. 4A). Macrophages isolated from the $P_{2\times7}R^{-/-}$ mice demonstrated the same low fluorescence in the absence and presence of extracellular ATP. In the presence of saponin, a detergent that permeabilizes the plasma membrane, YoPro Yellow accumulates to the same extent in the both wild-type and $P_{2\times7}R^{-/-}$ macrophages (FIG. 4B). Therefore, the knockout of the $P_{2\times7}R$ is associated with loss of ATP-dependent YoPro Yellow accumulation.

Stimulus-Coupled IL-1β Posttranslational Processing

Figure 5A:
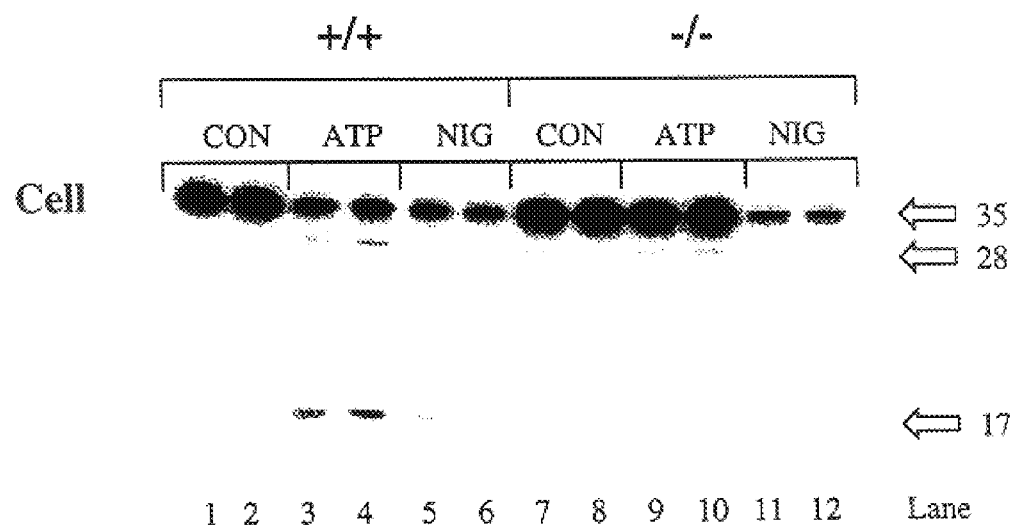
FIGS. 5A and 5B are representations of an autoradiograph which demonstrates stimulus-coupled IL-1β posttranslational processing in $P_{2\times7}R^{+/+}$ and $P_{2\times7}R^{-/-}$ macrophages. Peritoneal macrophages isolated from $P_{2\times7}R^{+/+}$ and $P_{2\times7}R^{-/-}$ mice were stimulated with lipopolysaccharide (LPS), radiolabeled with $^{35}$S-methionine, and stimulated with 5 mM ATP, 20 μM nigericin, or no effector, for 30 minutes. The supernatant (FIG. 5B) and macrophages (FIG. 5A) were harvested independently and the samples were immunoprecipitated for IL-1β. Immunoprecipitates were electrophoresed on an SDS-polyacrylamide gel, from which an autoradiograph was developed.
Figure 5B:
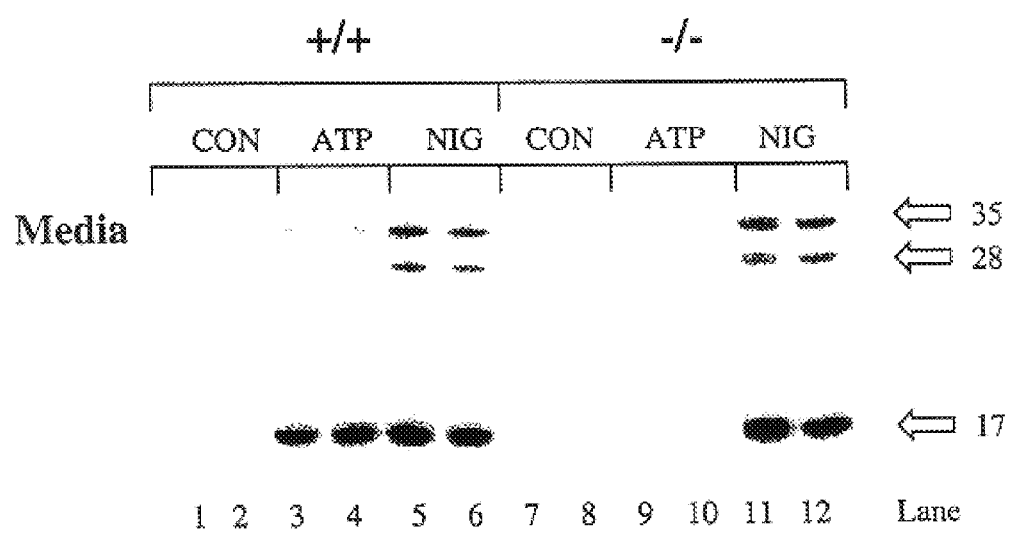

Peritoneal macrophages isolated from wild-type and $P_{2\times7}R^{-/-}$ mice were stimulated with LPS and labeled with [$^{35}$S]methionine. These radiolabeled cells then were cultured in the absence or presence of a secretory stimulus, after which cells and media were harvested separately, cells were solubilized by detergent extraction, and IL-1β was recovered from the media and cell extracts by immunoprecipitation. Radiolabeled 35 kDa proIL-1β was recovered from cell extracts derived from both wild-type and $P_{2\times7}R^{-/-}$ macrophages (FIGS. 5A and 5B). The amount of [$^{35}$S]methionine recovered as the cell-associated 35 kDa polypeptide after the chase in the absence of a secretory stimulus was 43,900 PSL/LDH eq and 44,100 PSL/LDH eq, respectively, from the wild-type and knockout macrophages. This similarity suggests that the two cell-types generated comparable amounts of proIL-1β in response to LPS activation. Neither the wild-type nor the $P_{2\times7}R^{-/-}$ macrophages released radiolabeled IL-1β to the medium in the absence of a secretory stimulus (FIG. 5B).

Figure 6A:
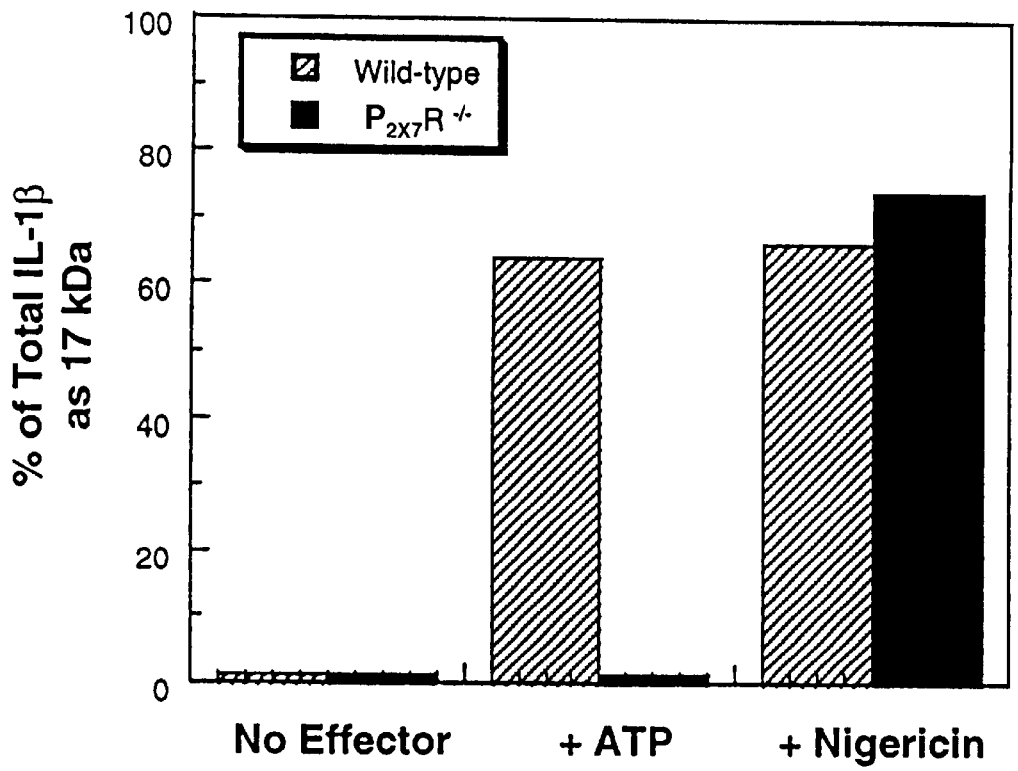
FIG. 6A is a graphic representation showing the percentage of IL-1β posttranslational processing in $P_{2\times7}R^{+/+}$ and $P_{2\times7}R^{-/-}$ macrophages. Peritoneal macrophages isolated from $P_{2\times7}R^{+/+}$ and $P_{2\times7}R^{-/-}$ mice were stimulated with LPS, radiolabeled with $^{35}$S-methionine, and stimulated with 5 mM ATP, or 20 μM nigericin, or without an effector, for 30 minutes. The supernatant and macrophages were harvested independently and the samples were immunoprecipitated for IL-1β. Immunoprecipitates were run on an SDS-polyacrylamide gel and the quantity of radioactivity associated with an individual IL-1β polypeptide species was determined by scanning dried gels with a phosphoimager. This figure depicts the percentage of the total radiolabeled IL-1β recovered as the 17 kDa IL-1β polypeptide.
Figure 6B:
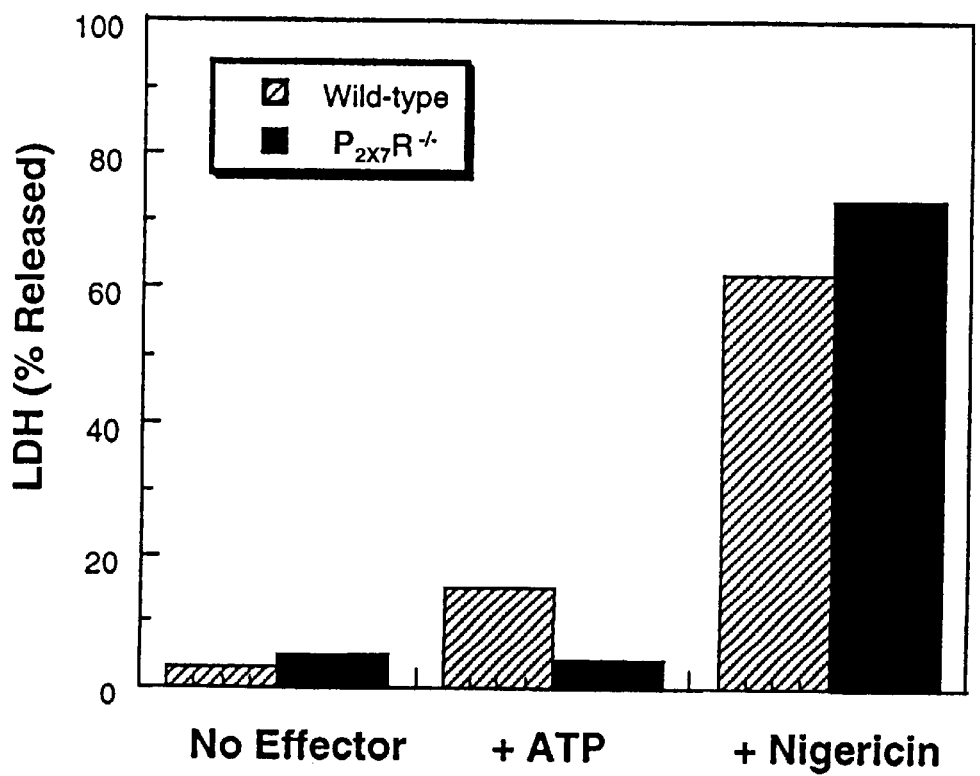
FIG. 6B is a graphic representation showing the percentage of lactate dehydrogenase (LDH) released from the total culture associated LDH in the samples described in FIG. 6A.

Treatment of LPS-activated/[$^{35}$S] methionine-labeled wild-type macrophages with extracellular ATP promoted formation and release of 17 kDa IL-1β (FIG. 5B). Cytokine that remained cell-associated was, for the most part, recovered as the 35 kDa procytokine (FIG. 5A). After correcting for the 2-fold loss of radioactivity that occurs when the 35 kDa procytokine is proteolytically processed by caspase-1, the extracellular 17 kDa polypeptide represents 64% of the total (sum of cell-associated and media species) radiolabeled IL-1β recovered from these cultures (FIG. 6A). In sharp contrast, LPS-activated/[$^{35}$S]methionine-labeled $P_{2x7}R^{-/-}$ macrophages did not release any radiolabeled IL-1β to the medium in response to ATP (FIG. 5B). Moreover, cytokine recovered from extracts of the ATP-treated $P_{2x7}R^{-/-}$ macrophages persisted as the 35kDa procytokine species (FIG. 5A). ATP-treated wild-type, but not knockout, macrophages demonstrated enhanced release of cytoplasmic enzyme lactate dehydrogenase (LDH) relative to non-ATP treated cultures (FIG. 6B).

In response to the potassium ionophore nigericin, on the other hand, both wild-type and $P_{2x7}R^{-/-}$ macrophages produced and released 17 kDa IL-1β (FIG. 5B). The extracellular mature cytokine represented 66% and 74%, respectively, of the total [$^{35}$S]methionine-labeled IL-1β recovered from the wild-type and $P_{2x7}R^{-/-}$ cultures (FIG. 6A). Moreover, both macrophage populations released comparable quantities of LDH in response to nigericin (FIG. 6B). Thus, $P_{2x7}R^{-/-}$ macrophages produce proIL-1β in response to LPS challenge, and they posttranslationally process this procytokine in response to nigericin stimulation. However, as a result of the absence of the $P_{2x7}R$, these cells do not produce or release mature IL-1β in response to ATP challenge.

Characterization of In Vivo Cytokine Production Capabilities

Figure 7:
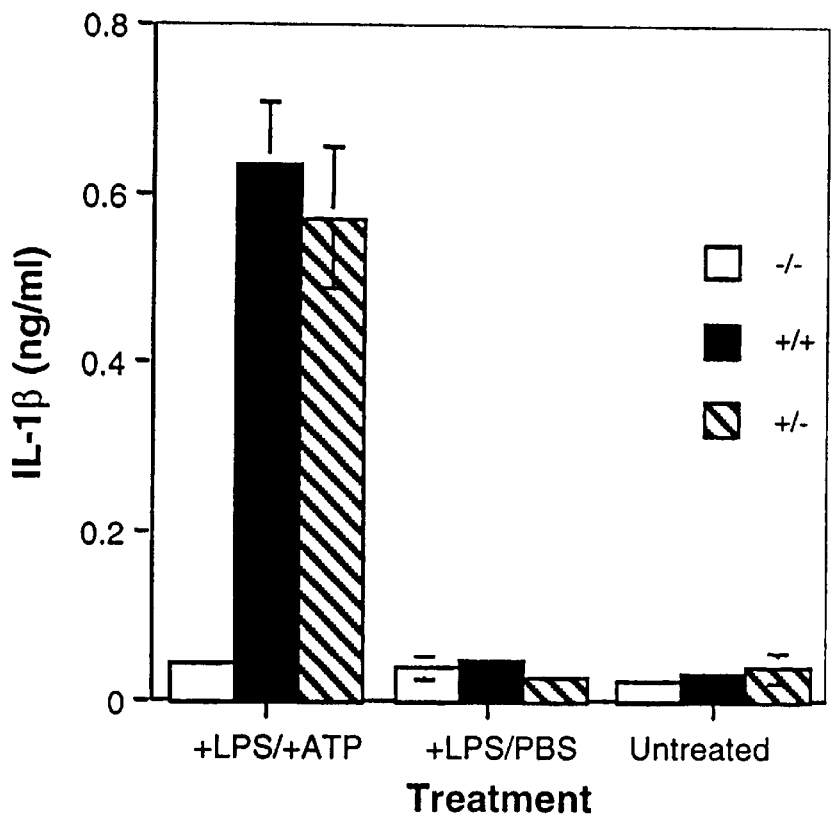
FIG. 7 is a graphic representation showing the abolishment of ATP-induced IL-1β release in $P_{2\times7}R^{-/-}$ mice. Mice were either injected i.p. with LPS or left untreated. Two hours later, phosphate buffered saline (10 mM phosphate, 150 mM NaCl) (PBS) or ATP was injected i.p. into LPS-primed mice. Following an additional 30 minute incubation, the peritoneal cavity was lavaged and the amount of IL-1β recovered was measured by ELISA.

Peritoneal macrophages exposed to LPS in vivo also require a secretion stimulus to elicit efficient externalization of mature IL-1β (Griffiths et al. (1995) J. Immunol. 154:2821–2828). To determine whether absence of the $P_{2x7}R$ affects this behavior, mice were primed with LPS, and 2 hours later they received an ip injection of PBS with or without ATP. Peritoneal lavage fluids from these mice then were assessed for IL-1β content by ELISA. Wild-type LPS-primed animals yielded no significant IL-1β in response to PBS (FIG. 7), but abundant quantities of IL-1β were detected following ATP challenge (FIG. 7). A similar pattern was observed in mice heterozygous for the $P_{2x7}R$ disruption (+/−) (FIG. 7). In contrast, LPS-primed $P_{2x7}R^{-/-}$ mice failed to generate significant levels of IL-1β in response to ATP challenge (FIG. 7).

Figure 8:
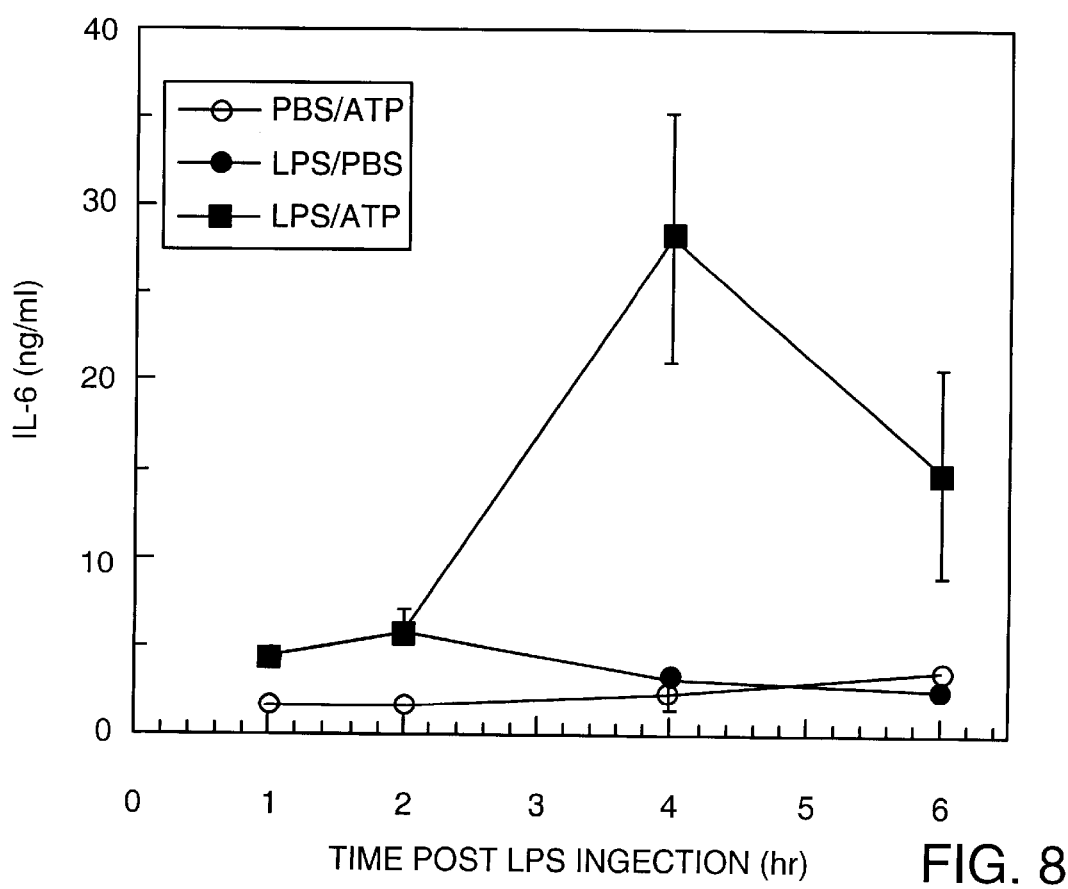
FIG. 8 is a graphic representation showing ATP-induced IL-6 release in LPS primed mice. Wild-type mice were primed by an injection of LPS (or PBS) at time 0. Two hours later an injection of ATP (or PBS) was administered to promote IL-1 posttranslational processing and the mice were incubated for an additional 4 hours. Peritoneal lavages were collected at several times during the course of the experiment and analyzed for IL-6 by ELISA.

As noted earlier, IL-1 signaling often leads to the production of other cytokines such as IL-6 (Allen et al. (2000) J. Exp. Med. 191:859–869). To demonstrate this cascade effect, mice were primed by an injection of LPS (or phosphate buffered saline) at time 0. Two hours later an injection of ATP (or PBS) was administered to promote IL-1 posttranslational processing and the mice were incubated for an additional 4 hours. Peritoneal lavages were collected at several times during the course of the experiment and analyzed for IL-6 by ELISA. Samples recovered from wild-type mice subjected to an initial priming injection of PBS followed 2 hours later by ATP did not contain significant levels of IL-6 at any time (FIG. 8). Mice that received an initial priming injection of LPS followed by PBS yielded levels of IL-6 at 1 and 2 hours (4 to 5 ng/ml) that were elevated above those recovered from mice injected with the combination of phosphate buffered saline and ATP (FIG. 8). By 4 hours, however, IL-6 levels recovered from the LPS-PBS treated animals returned to baseline (FIG. 9). On the other hand, LPS-primed mice that subsequently were challenged with ATP demonstrated a dramatic increase in lavage fluid IL-6, reaching a peak value >25 ng/ml at the 4 hour time point (FIG. 8).

Wild-type and $P_{2x7}R^{-/-}$ mice were compared in this two stage production assay format to determine whether absence of the receptor altered IL-6 production. Mice were administered a priming ip injection of LPS followed 2 hours later by a PBS or ATP challenge. Peritoneal lavage fluids subsequently were collected at 30 and 120 minutes and these were assessed for cytokine content by ELISA. Wild-type mice primed with an intraperitoneal injection of LPS and challenged with an intraperitoneal injection of PBS or ATP for 30 minutes yielded 0.02 ng/ml and 0.4 ng/ml of IL-1β, respectively (Table 1). When the time of the challenge reaction was extended to 2 hours, IL-1β levels declined slightly to 0.34 ng/ml in the ATP-treated mice, but levels of IL-1β within lavage fluids recovered from PBS challenged mice remained at the lower limit of detection (Table 1). Minimal levels of IL-1β also were recovered from $P_{2x7}R^{-/-}$ mice challenged with PBS, and ATP challenge did not augment production of IL-1β by these mice at either the 30 minute or 120 minute time point (Table 1). Quantities of IL-6 generated by wild-type and knockout animals in response to PBS challenge were comparable at the 30 minute harvest, representing 6 ng/ml and 5 ng/ml, respectively (Table 1). After 120 minutes of PBS challenge, IL-6 levels declined in both sets of animals to baseline values (Table 1). After 30 minutes of ATP challenge, both wild-type and $P_{2x7}R^{-/-}$ mice yielded 8 to 9 ng/ml of IL-6; these values are slightly elevated over the quantities of IL-6 recovered from the PBS challenged animals at 30 minutes (Table 1). After 120 minutes of ATP challenge, on the other hand, wild-type animals yielded greater levels of IL-6 (17 ng/ml) than did the $P_{2x7}R^{-/-}$ mice (6 ng/ml) (Table 1). Although levels of IL-6 generated at this time by the ATP-challenged knockout animals were lower than those generated by their wild-type counterparts, they were elevated above those generated in response to PBS challenge (6 ng/ml when challenged with ATP versus 0 ng/mi when challenged with PBS, Table 1). This suggests that ATP affects IL-6 production via both a $P_{2x7}R$-dependent and -independent mechanism Animals that were not primed with LPS yielded lavage fluids totally devoid of IL-1 and IL-6. Values in Table 1 represent the mean±standard deviation (N=6).

TABLE 1

|  | PBS Challenge | | | | ATP Challenge | | | |
| --- | --- | --- | --- | --- | --- | --- | --- | --- |
|  | IL-1 (ng/ml) | | IL-6 (ng/ml) | | IL-1 (ng/ml) | | IL-6 (ng/ml) | |
| Time Post Challenge (min) | WT | $P_{2x7}R^{-/-}$ | WT | $P_{2x7}R^{-/-}$ | WT | $P_{2x7}R^{-/-}$ | WT | $P_{2x7}R^{-/-}$ |
| 30 | 0.05 | 0.04 | 5.6 ± 0.7 | 4.7 = 0.6 | 0.4 ± 0.12 | 0.04 | 8.2 ± 1.7 | 9 ± 1 |
| 120 | 0.02 | 0.02 | 1 ± 0.6 | 0 | 0.33 ± 0.08 | 0.02 | 16.8 ± 2.3 | 5.7 = 1.2 |

EQUIVALENTS

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A transgenic mouse whose genome comprises a homozygous disruption of the $P_{2\times7}$ receptor ($P_{2\times7}R$) gene, wherein the mouse lacks a functional endogenous $P_{2\times7}R$ and wherein the mouse exhibits a phenotype of reduced ATP-stimulated IL-α, IL-β, or IL-18 post-translational processing, or reduced ATP-stimulated IL-6 production, or reduced ATP-stimulated intracellular accumulation of macromolecules.

2. A cultured mouse embryonic stem cell, whose genome comprises a homozygous disruption of the $P_{2\times7}$ receptor ($P_{2\times7}R$) gene, wherein the cell lacks functional endogenous $P_{2\times7}R$ and wherein said cell exhibits a phenotype of reduced ATP-stimulated IL-α, IL-β, or IL-18 post-translational processing, or reduced ATP stimulated IL-6 production, or reduced ATP-stimulated intracellular accumulation of macromolecules, used to make the mouse of claim 1.

3. A cultured mouse cell whose genome comprises a homozygous disruption of the $P_{2\times7}$ receptor ($P_{2\times7}R$) gene, wherein the cell lacks a functional endogenous $P_{2\times7}R$ and wherein said cell exhibits a phenotype of reduced ATP-stimulated IL-α, IL-β, or IL-18 post-translational processing, or reduced ATP-stimulated IL-6 production, or reduced ATP-stimulated intracellular accumulation of macromolecules.

4. The mouse cell of claim 3, wherein the cell is isolated from a transgenic mouse or transgenic mouse embryo whose genome comprises a homozygous disruption of the $P_{2\times7}$ receptor ($P_{2\times7}R$) gene, wherein the mouse or mouse embryo lacks a functional endogenous $P_{2\times7}R$ and wherein the mouse or mouse embryo exhibits a phenotype of reduced ATP-stimulated IL-α, IL-β, or IL-18 post-translational processing, or reduced ATP-stimulated IL-6 production, or reduced ATP-stimulated intracellular accumulation of macromolecules.

5. A method for producing a mouse whose genome comprises a homozygous disruption of the $P_{2\times7}R$ gene, the method comprising:

a) introducing a DNA sequence into mouse ES cells, wherein the DNA sequence inserts a disruption into the $P_{2\times7}R$ gene;

b) selecting those mouse ES cells whose genome comprise a disruption of the $P_{2\times7}R$ gene;

c) introducing an ES cell selected in step b) in a mouse blastocyst;

d) transplanting the blastocyst of step c) into a pseudopregnant mouse;

e) developing the transferred blastocyst to term to produce a chimeric mouse; and f) mating sexually mature chimeric mice to obtain a mouse homozygous for a disruption of the $P_{2\times7}R$ gene, wherein said homozygous gene disruption results in a phenotype of reduced ATP-stimulated IL-α, IL-β, or IL-18 post-translational processing, or reduced ATP-stimulated IL-6 production, or reduced ATP-stimulated intracellular accumulation of macromolecules.

6. An isolated nucleic acid molecule comprising a $P_{2\times7}R$ gene targeting construct, wherein, upon introduction of said construct into a cell, said targeting construct recombines with a $P_{2\times7}R$ gene in the cellular genome of said cell, thereby inserting itself into the genome at the $P_{2\times7}R$ gene locus and disrupting $P_{2\times7}R$ gene function in said cell, wherein said cell exhibits reduced ATP-stimulated IL-α, IL-β, or IL-18 post-translational processing, or reduced ATP-stimulated IL-6 production, or reduced ATP-stimulated intracellular accumulation of macromolecules.

\* \* \* \* \*

UNITED STATES PATENT AND TRADEMARK OFFICE
CERTIFICATE OF CORRECTION

PATENT NO. : 6,677,501 B2  Page 1 of 1
DATED : January 13, 2004
INVENTOR(S) : Gabel et al.

It is certified that error appears in the above-identified patent and that said Letters Patent is hereby corrected as shown below:

<u>Column 27,</u>
Lines 33, 40 48 and 57, replace "IL-α" with -- IL-1-∝ --;

<u>Column 28,</u>
Line 46 and 55, replace "IL-α" with -- IL-1-∝ --.

Signed and Sealed this

Twenty-seventh Day of April, 2004

JON W. DUDAS
*Acting Director of the United States Patent and Trademark Office*